(12) United States Patent
Seiberg et al.

(10) Patent No.: US 7,879,823 B2
(45) Date of Patent: *Feb. 1, 2011

(54) TOPICAL ANTI-CANCER COMPOSITIONS AND METHODS OF USE THEREOF

(75) Inventors: Miri Seiberg, Princeton, NJ (US); Stanley S. Shapiro, Roseland, NJ (US); Christine Paine, Hoboken, NJ (US); Allan H. Conney, Princeton, NJ (US); Mou-Tuan Huang, Englewood Cliffs, NJ (US)

(73) Assignee: Johnson & Johnson Consumer Companies, Skillman, NJ (US)

(*) Notice: Subject to any disclaimer, the term of this patent is extended or adjusted under 35 U.S.C. 154(b) by 1061 days.

This patent is subject to a terminal disclaimer.

(21) Appl. No.: 10/885,324

(22) Filed: Jul. 6, 2004

(65) Prior Publication Data

US 2004/0247713 A1  Dec. 9, 2004

Related U.S. Application Data

(60) Division of application No. 10/108,248, filed on Mar. 27, 2002, now Pat. No. 7,309,688, which is a continuation-in-part of application No. 09/698,454, filed on Oct. 27, 2000.

(60) Provisional application No. 60/201,494, filed on May 3, 2000, provisional application No. 60/163,906, filed on Nov. 5, 1999.

(51) Int. Cl.
A01N 37/18 (2006.01)
A01N 65/00 (2006.01)
A61K 8/00 (2006.01)
A61K 8/18 (2006.01)
A61K 8/02 (2006.01)
A61K 9/127 (2006.01)
A61K 36/48 (2006.01)
A61Q 17/04 (2006.01)

(52) U.S. Cl. .......................... 514/59; 424/59; 424/401; 424/450; 424/757; 514/887

(58) Field of Classification Search ................ 514/2, 514/59, 887; 424/59, 401, 450, 757
See application file for complete search history.

(56) References Cited

U.S. PATENT DOCUMENTS 2,876,164 A   3/1959   Wershaw (Continued)

FOREIGN PATENT DOCUMENTS

CN   1081899   2/1994

(Continued)

OTHER PUBLICATIONS

Robert L. Anderson and Walter J. Wolf, Compositional changes in trypsin inhibitors, phytic acid, saponins, and isoflavones related to soybean processing; J. Nutr. 125:581S-588S, 1995.*

(Continued)

*Primary Examiner*—Frederick Krass
*Assistant Examiner*—Benjamin Packard
(74) *Attorney, Agent, or Firm*—Dann, Dorfman, Herrell & Skillman; Robert C. Netter, Jr.; Kathleen D. Rigaut

(57) ABSTRACT

Described are skin-care compositions containing non denatured soy products and optionally other anti-cancer or anti-aging agents. The compositions can be applied topically to reduce the risk of UV-induced cutaneous tumors.

17 Claims, 8 Drawing Sheets

U.S. PATENT DOCUMENTS

| | | |
|---|---|---|
| 3,097,947 A | 7/1963 | Kemmerer |
| 3,625,976 A | 12/1971 | Theimer |
| 3,755,560 A | 8/1973 | Dickert |
| 4,007,266 A | 2/1977 | Choay |
| 4,056,637 A | 11/1977 | Hagiwara et al. |
| 4,151,304 A | 4/1979 | Evans |
| 4,190,671 A | 2/1980 | Vanstone |
| 4,219,569 A | 8/1980 | Glenn |
| 4,223,018 A | 9/1980 | Belle |
| 4,254,105 A | 3/1981 | Fukuda |
| 4,272,544 A | 6/1981 | Cella |
| 4,278,570 A | 7/1981 | Flom |
| 4,279,930 A | 7/1981 | Hall |
| 4,297,348 A | 10/1981 | Frazier |
| 4,331,692 A | 5/1982 | Drevici |
| 4,333,927 A | 6/1982 | Ofuchi |
| 4,368,187 A | 1/1983 | Flom |
| 4,370,315 A | 1/1983 | Greff |
| 4,382,960 A | 5/1983 | Flom |
| 4,386,067 A | 5/1983 | Guillon |
| 4,421,769 A | 12/1983 | Dixon |
| 4,427,670 A | 1/1984 | Ofuchi |
| 4,434,095 A | 2/1984 | Chipens et al. |
| 4,437,895 A | 3/1984 | Koulbanis |
| 4,439,418 A | 3/1984 | Moller |
| 4,462,981 A | 7/1984 | Smith |
| 4,477,434 A | 10/1984 | Kosaka |
| 4,486,448 A | 12/1984 | Ser |
| 4,488,564 A | 12/1984 | Grollier |
| 4,512,973 A | 4/1985 | Dennis |
| 4,515,778 A | 5/1985 | Kastell |
| 4,524,067 A | 6/1985 | Arichi |
| 4,537,782 A | 8/1985 | Millet |
| 4,550,035 A | 10/1985 | Smith |
| 4,578,267 A | 3/1986 | Salamone |
| 4,584,190 A | 4/1986 | Tejima |
| 4,603,146 A | 7/1986 | Kligman |
| 4,604,281 A | 8/1986 | Deckner |
| 4,612,192 A | 9/1986 | Scheuffgen |
| 4,690,821 A | 9/1987 | Smith |
| 4,707,293 A | 11/1987 | Ferro |
| 4,727,088 A | 2/1988 | Scott et al. |
| 4,760,096 A | 7/1988 | Sakai |
| 4,793,991 A | 12/1988 | Slimak |
| 4,824,662 A | 4/1989 | Hofmann |
| 4,834,076 A | 5/1989 | Millet |
| 4,847,267 A | 7/1989 | Deckner |
| 4,851,214 A | 7/1989 | Walters |
| 4,859,458 A | 8/1989 | Salamone |
| 4,867,964 A | 9/1989 | Forestier |
| 4,871,530 A | 10/1989 | Grollier |
| 4,885,169 A | 12/1989 | Gazzani |
| 4,895,839 A | 1/1990 | Bombardelli |
| 4,906,457 A * | 3/1990 | Ryan ........................... 424/59 |
| 4,943,462 A | 7/1990 | Komerska |
| 4,960,588 A | 10/1990 | Hoshowski |
| 4,960,764 A | 10/1990 | Figueroa |
| 4,970,216 A | 11/1990 | Deckner |
| 4,971,825 A | 11/1990 | Kitazume et al. |
| 4,978,528 A | 12/1990 | Degre |
| 5,002,761 A | 3/1991 | Mueller |
| 5,006,337 A | 4/1991 | Motitschke et al. |
| 5,032,382 A | 7/1991 | Grollier |
| 5,032,400 A | 7/1991 | Wiersum |
| 5,043,323 A | 8/1991 | Bombardelli |
| 5,057,417 A | 10/1991 | Hammonds et al. |
| 5,077,038 A | 12/1991 | Hofmann |
| 5,077,040 A | 12/1991 | Bergmann |
| 5,104,655 A | 4/1992 | Bombardelli |
| 5,110,603 A | 5/1992 | Rau |
| 5,116,605 A | 5/1992 | Alt |
| 5,118,671 A | 6/1992 | Bombardelli |
| 5,130,142 A | 7/1992 | Wong et al. |
| 5,147,859 A | 9/1992 | Bombardelli |
| 5,166,139 A | 11/1992 | Bombardelli |
| 5,171,577 A | 12/1992 | Griat |
| 5,179,091 A | 1/1993 | Lesieur |
| 5,188,823 A | 2/1993 | Shapiro |
| 5,192,332 A | 3/1993 | Lang |
| 5,194,252 A | 3/1993 | Hofmann |
| 5,217,717 A * | 6/1993 | Kennedy et al. ............ 424/757 |
| 5,229,104 A | 7/1993 | Sottery |
| 5,231,090 A | 7/1993 | Hsia |
| 5,248,495 A | 9/1993 | Patterson |
| 5,254,331 A | 10/1993 | Mausner |
| 5,260,065 A | 11/1993 | Mathur |
| 5,270,042 A | 12/1993 | Whitham |
| 5,276,058 A | 1/1994 | Satoh |
| 5,306,444 A | 4/1994 | Kitamura |
| 5,310,734 A | 5/1994 | Losch |
| 5,322,839 A | 6/1994 | Voegeli |
| 5,352,443 A | 10/1994 | Kubo |
| 5,362,494 A | 11/1994 | Zysman |
| 5,364,886 A | 11/1994 | Loliger |
| 5,393,519 A | 2/1995 | Dowell |
| 5,397,497 A | 3/1995 | Jakobson |
| 5,407,675 A | 4/1995 | Etemad-Moghadam |
| 5,411,742 A | 5/1995 | Sebag |
| 5,427,814 A | 6/1995 | Loliger |
| 5,428,026 A | 6/1995 | Colarow |
| 5,438,044 A | 8/1995 | Losch |
| 5,439,672 A | 8/1995 | Zabotto |
| 5,443,839 A | 8/1995 | Meybeck |
| 5,443,840 A | 8/1995 | Morancais |
| 5,444,092 A | 8/1995 | Collins |
| 5,446,605 A | 8/1995 | Umehara |
| 5,466,452 A | 11/1995 | Whittle |
| 5,468,473 A | 11/1995 | Mullen |
| 5,498,420 A | 3/1996 | Mentrup |
| 5,503,832 A | 4/1996 | De Stoutz |
| 5,505,946 A | 4/1996 | Kennedy et al. |
| 5,510,391 A | 4/1996 | Elson |
| 5,523,308 A | 6/1996 | Costanzo |
| 5,539,129 A | 7/1996 | Zysman |
| 5,545,399 A | 8/1996 | Lee |
| 5,547,661 A | 8/1996 | Sun |
| 5,554,647 A | 9/1996 | Perricone |
| 5,565,439 A * | 10/1996 | Piazza et al. ................ 514/110 |
| 5,565,493 A | 10/1996 | Nakata et al. |
| 5,567,420 A | 10/1996 | McEleney |
| 5,569,663 A | 10/1996 | Ribier |
| 5,571,503 A | 11/1996 | Mausner |
| 5,578,297 A | 11/1996 | Mellul |
| 5,589,181 A | 12/1996 | Bencsits |
| 5,595,984 A | 1/1997 | Blank |
| 5,597,814 A | 1/1997 | Blank |
| 5,601,833 A | 2/1997 | Roboer |
| 5,603,949 A | 2/1997 | Meybeck |
| 5,605,894 A | 2/1997 | Blank |
| 5,607,666 A | 3/1997 | Masson |
| 5,607,692 A | 3/1997 | Ribier |
| 5,614,180 A | 3/1997 | Chung |
| 5,614,215 A | 3/1997 | Ribier |
| 5,616,572 A | 4/1997 | Blank |
| 5,618,522 A | 4/1997 | Kaleta |
| 5,620,692 A | 4/1997 | Potter |
| 5,622,690 A | 4/1997 | Potter |
| 5,626,868 A | 5/1997 | Morancais |
| 5,629,015 A | 5/1997 | Ribier |
| 5,629,301 A | 5/1997 | Blank |
| 5,631,318 A | 5/1997 | Ito |
| 5,635,165 A | 6/1997 | Panitch |
| 5,637,316 A | 6/1997 | Ribier |
| 5,639,785 A | 6/1997 | Kung |

| | | | | | | |
|---|---|---|---|---|---|---|
| 5,641,509 A | 6/1997 | Gross | | 5,962,414 A | 10/1999 | Birk |
| 5,643,583 A | 7/1997 | Voultoury | | 5,962,441 A | 10/1999 | Blank |
| 5,643,587 A | 7/1997 | Scancarella | | 5,965,153 A | 10/1999 | Allen |
| 5,643,601 A | 7/1997 | Gross | | 5,972,355 A | 10/1999 | Knight et al. |
| 5,650,166 A | 7/1997 | Ribier | | 5,981,450 A | 11/1999 | Fabry |
| 5,652,230 A | 7/1997 | Blank | | 5,985,338 A | 11/1999 | Suh |
| 5,653,988 A | 8/1997 | Gerber | | 5,985,809 A | 11/1999 | Frankenbach |
| 5,660,853 A | 8/1997 | Hansenne-Richoux | | 5,990,291 A | 11/1999 | Waggle |
| 5,665,367 A | 9/1997 | Burger | | 6,001,367 A | 12/1999 | Bazin et al. |
| 5,670,547 A | 9/1997 | Milstein et al. | | 6,004,558 A | 12/1999 | Thurn et al. |
| 5,674,511 A | 10/1997 | Kacher | | 6,004,915 A | 12/1999 | Elliott |
| 5,676,935 A | 10/1997 | Mellul | | 6,013,250 A | 1/2000 | Cannell |
| 5,676,956 A | 10/1997 | Duffy | | 6,013,255 A | 1/2000 | Edens |
| 5,679,374 A | 10/1997 | Fanchon | | 6,017,549 A | 1/2000 | Knight et al. |
| 5,681,571 A | 10/1997 | Homgren et al. | | 6,017,893 A | 1/2000 | Segelman |
| 5,681,852 A | 10/1997 | Bissett | | 6,018,001 A | 1/2000 | Hiratani et al. |
| 5,683,683 A | 11/1997 | Scafidi | | 6,019,962 A | 2/2000 | Rabe |
| 5,686,102 A | 11/1997 | Gross | | 6,030,931 A | 2/2000 | Vinski |
| 5,688,763 A | 11/1997 | Hammonds, Jr. et al. | | 6,033,680 A | 3/2000 | Dixon |
| 5,691,327 A | 11/1997 | Blank | | 6,045,779 A | 4/2000 | Mueller |
| 5,712,356 A | 1/1998 | Bothe et al. | | 6,048,520 A | 4/2000 | Hoshowski |
| 5,723,148 A | 3/1998 | Love | | 6,051,602 A | 4/2000 | Bissett |
| 5,741,496 A | 4/1998 | Khaiat | | 6,054,137 A | 4/2000 | Breton |
| 5,753,612 A | 5/1998 | Mitrani | | 6,060,070 A | 5/2000 | Gorbach |
| 5,755,814 A | 5/1998 | Berg | | 6,063,398 A | 5/2000 | Gueret |
| 5,762,916 A | 6/1998 | Ansmann | | 6,080,393 A | 6/2000 | Liu et al. |
| 5,766,628 A | 6/1998 | Nurnberg | | 6,089,452 A | 7/2000 | Seiberg et al. |
| 5,776,917 A | 7/1998 | Blank | | 6,093,411 A | 7/2000 | Bissett |
| 5,780,456 A | 7/1998 | Blank | | 6,096,327 A | 8/2000 | Lezdey et al. |
| 5,780,457 A | 7/1998 | Blank | | 6,126,933 A * | 10/2000 | Warne et al. ............... 424/85.2 |
| 5,780,458 A | 7/1998 | Blank | | 6,180,662 B1 | 1/2001 | Lanzendorfer |
| 5,780,459 A | 7/1998 | Blank | | 6,183,761 B1 | 2/2001 | Bissett |
| 5,786,345 A | 7/1998 | Blank | | 6,183,762 B1 | 2/2001 | Deckers et al. |
| 5,786,346 A | 7/1998 | Blank | | 6,248,350 B1 | 6/2001 | Mori et al. |
| 5,789,396 A | 8/1998 | Blank | | 6,261,603 B1 | 7/2001 | McElwain |
| 5,795,879 A | 8/1998 | Blank | | 6,323,219 B1 | 11/2001 | Costanzo |
| 5,801,163 A | 9/1998 | Blank | | 6,399,083 B1 | 6/2002 | Pillai et al. |
| 5,804,216 A | 9/1998 | Terren | | 6,413,526 B1 | 7/2002 | Bazin et al. |
| 5,807,545 A | 9/1998 | Coffindaffer | | 6,423,747 B1 | 7/2002 | Lanzendörfer |
| 5,811,119 A | 9/1998 | Mehta et al. | | 6,433,025 B1 | 8/2002 | Lorenz |
| 5,824,702 A | 10/1998 | Wei | | 6,447,809 B1 | 9/2002 | Krumhar et al. |
| 5,833,965 A | 11/1998 | Sun | | 6,461,627 B1 | 10/2002 | Ichioka |
| 5,834,013 A | 11/1998 | Ribier | | 6,558,656 B2 | 5/2003 | Mann |
| 5,834,513 A | 11/1998 | Ptchelintsev | | 2002/0034489 A1 | 3/2002 | Wiegland |
| 5,840,717 A | 11/1998 | Blank | | 2002/0035046 A1 | 3/2002 | Lukenbach |
| 5,843,907 A | 12/1998 | Sakai et al. | | 2002/0065300 A1 | 5/2002 | Seiberg et al. |
| 5,843,926 A | 12/1998 | Blank | | 2002/0160061 A1 | 10/2002 | Saliou et al. |
| 5,863,546 A | 1/1999 | Swinehart | | 2002/0160062 A1 | 10/2002 | Liu et al. |
| 5,869,031 A | 2/1999 | Tarroux et al. | | 2002/0160063 A1 | 10/2002 | Miller et al. |
| 5,869,470 A | 2/1999 | Blank | | 2002/0182166 A1 | 12/2002 | Martin |
| 5,871,743 A | 2/1999 | Chajuss | | 2002/0192313 A1 | 12/2002 | Saliou et al. |
| 5,871,823 A | 2/1999 | Anders et al. | | 2002/0197244 A1 | 12/2002 | Seiberg et al. |
| 5,880,314 A | 3/1999 | Shinomiya | | 2003/0064048 A1 | 4/2003 | Seiberg et al. |
| 5,885,593 A | 3/1999 | Epstein | | 2003/0224075 A1 | 12/2003 | Liu et al. |
| 5,885,596 A | 3/1999 | Parab | | 2004/0009142 A1 | 1/2004 | Zambaux et al. |
| 5,885,600 A | 3/1999 | Blum | | 2004/0063593 A1 | 4/2004 | Wu et al. |
| 5,885,617 A | 3/1999 | Jordan | | 2004/0067244 A1 | 4/2004 | Friedman |
| 5,885,948 A | 3/1999 | Glenn | | 2005/0008665 A1 | 1/2005 | Batzer |
| 5,888,522 A | 3/1999 | Pickart | | 2005/0019279 A1 | 1/2005 | Goppel |
| 5,908,618 A | 6/1999 | Lorant | | 2005/0281776 A1 | 12/2005 | Courcoux |
| 5,912,175 A | 6/1999 | Wille, Jr. | | 2007/0009459 A1 | 1/2007 | Magnant |
| 5,916,577 A | 6/1999 | Golz | | 2007/0041931 A1 | 2/2007 | Morelli |
| 5,928,654 A | 7/1999 | Duranton | | 2007/0160564 A1 | 7/2007 | Liu et al. |
| 5,928,658 A | 7/1999 | Kishida | | | | |
| 5,928,889 A | 7/1999 | Bakich | | FOREIGN PATENT DOCUMENTS | | |
| 5,936,052 A | 8/1999 | Bothe et al. | | | | |
| 5,942,479 A | 8/1999 | Frankenbach | | CN | 1146876 | 4/1997 |
| 5,945,095 A | 8/1999 | Mougin | | CN | 1166960 | 12/1997 |
| 5,945,109 A | 8/1999 | Schmidt | | DE | 4432947 | 3/1996 |
| 5,952,373 A | 9/1999 | Lanzendorfer | | DE | 19634206 | 3/1998 |
| 5,958,387 A | 9/1999 | Bara | | DE | 19818849 A | 10/1998 |
| 5,961,980 A | 10/1999 | Kennedy | | EP | 0 532 465 A | 3/1993 |
| 5,962,015 A | 10/1999 | Delrieu | | EP | 581624 | 2/1994 |

| | | |
|---|---|---|
| EP | 582239 | 2/1994 |
| EP | 1 210 946 A | 6/2002 |
| EP | 1 348 441 A | 10/2003 |
| EP | 1 647 278 A | 4/2006 |
| GB | 1098951 A | 1/1968 |
| JP | 02-286165 A | 11/1990 |
| JP | 04283518 | 10/1992 |
| JP | 06-256156 A | 9/1994 |
| JP | 8143442 A | 6/1996 |
| JP | 10-046196 A | 2/1998 |
| JP | 10-139654 A | 5/1998 |
| JP | 10120542 | 5/1998 |
| JP | 10-175815 A | 6/1998 |
| JP | 410226642 | 8/1998 |
| JP | 2000-351720 A | 12/2000 |
| JP | 2001-271096 A | 10/2001 |
| JP | 2004-000019 A | 1/2004 |
| WO | WO 94/07462 A | 4/1994 |
| WO | 96/28008 | 9/1996 |
| WO | 96/29050 | 9/1996 |
| WO | 98/29091 | 7/1998 |
| WO | WO 9900110 | 7/1999 |
| WO | WO 9939682 | 8/1999 |
| WO | WO 00/74699 A | 12/2000 |
| WO | WO 01/29163 A | 4/2001 |
| WO | WO 01/34909 A | 5/2001 |
| WO | WO 02/07697 A | 1/2002 |
| WO | WO 02/064104 A | 8/2002 |
| WO | WO 02/067988 | 9/2002 |
| WO | WO 02/074280 A | 9/2002 |
| WO | WO 03/32941 A | 4/2003 |
| WO | WO 03/039502 | 5/2003 |
| WO | WO 2004/022024 | 3/2004 |
| WO | WO 2005/097216 | 10/2005 |

OTHER PUBLICATIONS

Kay et al. (J Biol Chem. Jun. 1976 10;251(11):3411-6). Abstract.*
Meggio et al. (J Biochem. Jul. 1979;86(1):261-4). Abstract.*
Tan-Wilson et al. (Plant Physiol. Jun. 1985;78(2):310-314). Abstract.*
Papastoitsis et al. (Plant Physiol. Aug. 1991;96(4):1086-1092). Abstract.*
Scarafoni et al. (Phytochemistry. Jun. 2008;69(9):1820-5. Epub May 10, 2008). Abstract.*
National Library of Medicine serach results for sotbean trypsin inhibitors.*
Bowman Birk Tryspin Inhibitor Search Results in CAS HCaPlus Database.*
Sessa et al. "Toasted Soybean Flour Components with Trypsin Inhibitor Activity", JAOCS, vol. 63, No. 6, Jun. 1986, pp. 784-788.*
Odani et al., "Studies on Soybean Trypsin Inhibitors", J. Biochem, vol. 83, No. 3, 1978, pp. 747-753.*
U.S. Appl. No. 10/611,100, filed Jul. 1, 2003, Halas et al.
U.S. Appl. No. 09/110,409, filed Jul 6, 1998, Seiberg et al.
U.S. Appl. No. 10/659,598, filed Sep. 10, 2003, Seiberg et al.
U.S. Appl. No. 09/206,249, filed Dec. 7, 1998, Seiberg et al.
U.S. Appl. No. 09/677,511, filed Spe. 29, 2000, Liu et al.
U.S. Appl. No. 09/621,565, filed Jul 20, 2000, Seiberg et al.
U.S. Appl. No. 10/434,309, filed May 8, 2003, Seiberg et al.
Printout from website: http://www.faqs.org/health/Sick-V1/Acne.html (7 sheets) (date shown on printed sheet: Oct. 31, 2006).
PENTAPHARM, Product "ELHIBIN®" product catalog.
PENTAPHARM, Product "ELHIBIN®" product catalog (1998).
Wenninger, et al, International Cosmetic Ingredient Dictionary and Handbook, 7th edition, vol. 2 (1997), "Soybean (Glycine Soja) Protein", pp. 1332-1333.
McGuire, J.S. "Activation of Epidermal Tyrosinase." Biochemical Communications, 40(5); 1084-1089 (1970).
Ogawa, "Current Problem of Research on Hair Growth Mechanisms and Hair Growth Promoters", Fragrance Journal, vol. 5, pp. 1-5 (1989).
Uniqema: "Pharmaceutical and Cosmetic Uses of Diolic Acids", Research Disclosure, Kenneth Mason Publications, Hampshire, GB, vol. 444, No. 77 Apr. 2001.
Huang et al: "Inhibitory Effect of Topical Applications of Nondenatured Soymilk on the Formation and Growth of UVB-Induced Skin Tumors", Oncology Research, vol. 14 (2004) pp. 387-397.
http://familydoctor.org/online/famdocen/home/common/cancer/risk/159.html.
Jolles et al., "Enzymic Processes and Vascular Changes in the Skin Radiation Reaction", Br. J. Radiol. (1996) 39:12-18.

* cited by examiner

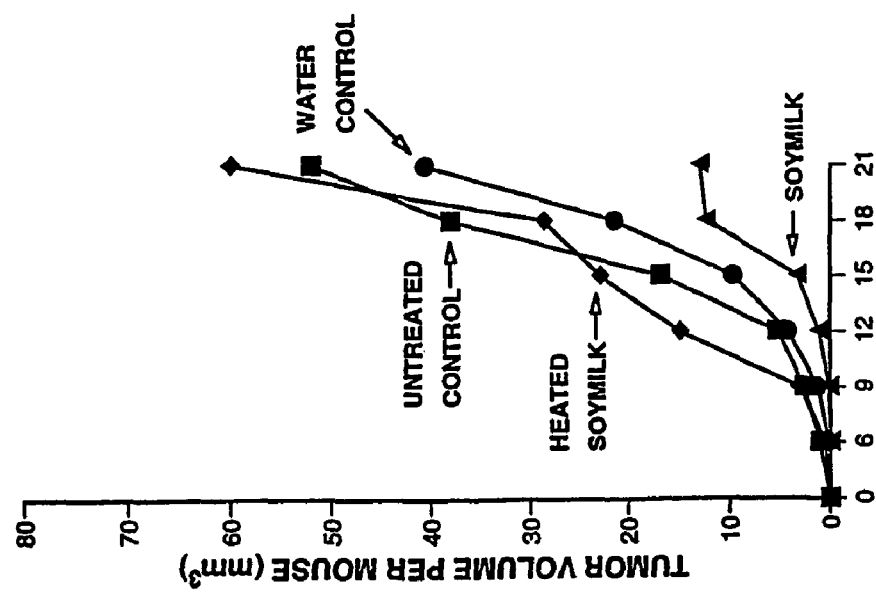
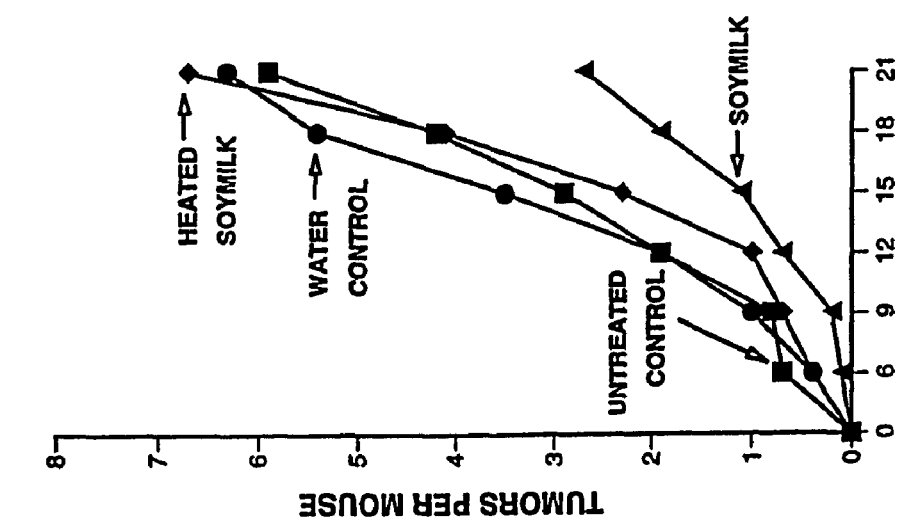
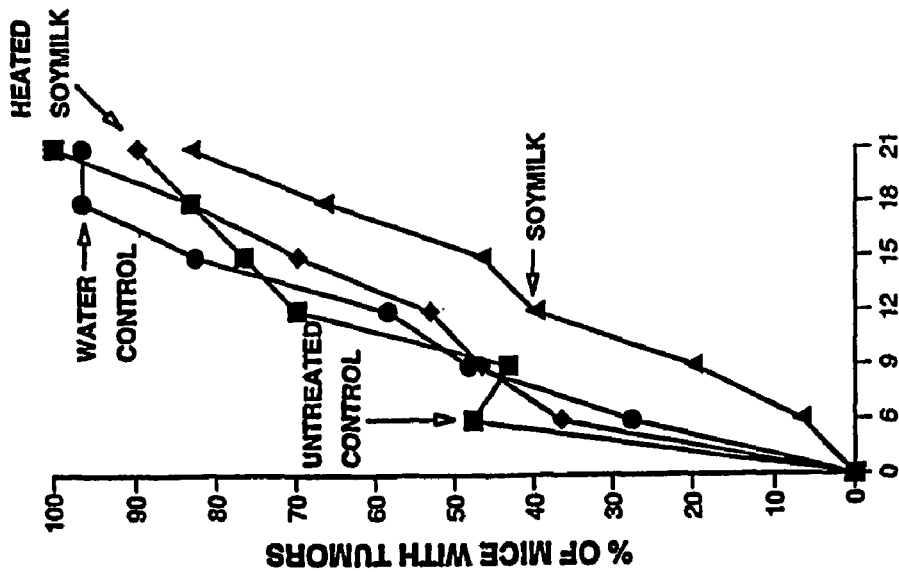
Fig. 2A
Fig. 2B
Fig. 2C

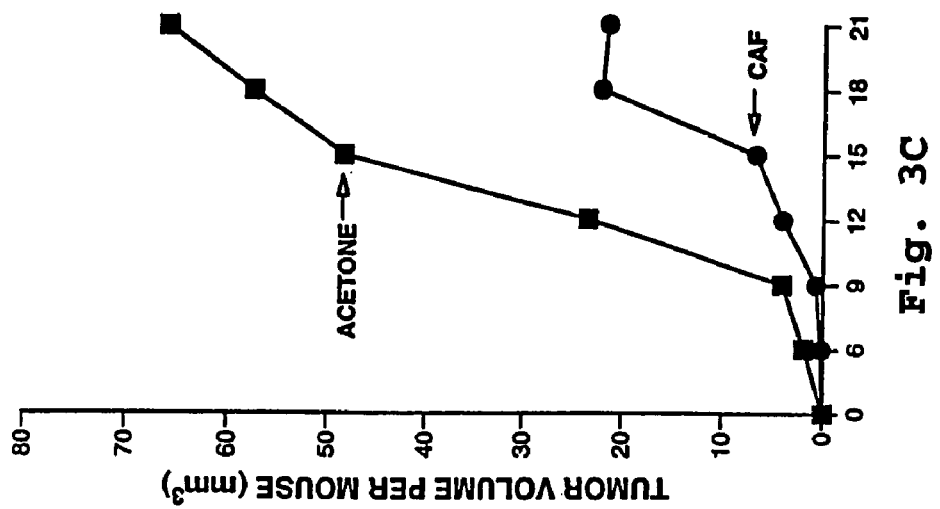
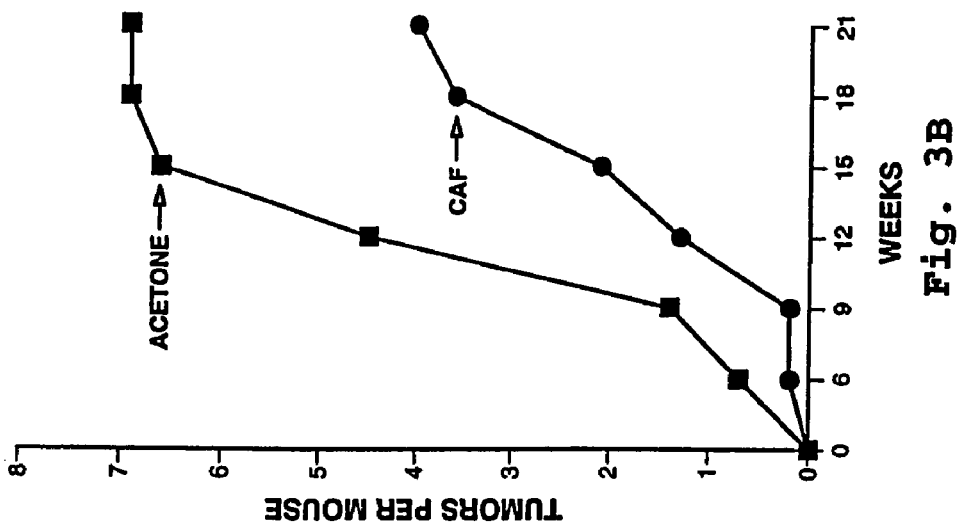
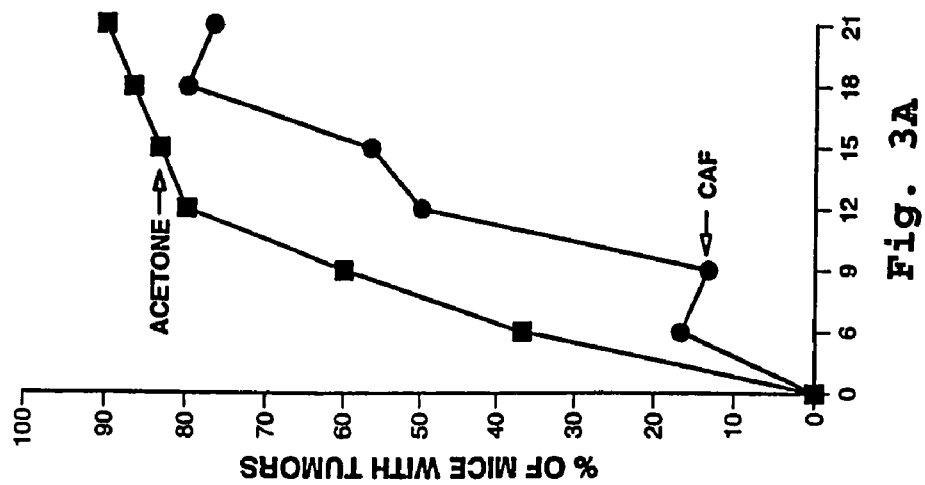

TOPICAL ANTI-CANCER COMPOSITIONS AND METHODS OF USE THEREOF

CROSS-REFERENCES TO RELATED APPLICATIONS

This application is a divisional application of U.S. patent application Ser. No. 10/108,248 filed Mar. 27, 2002, now U.S. Pat. No. 7,309,688, which is a continuation-in-part of U.S. patent application Ser. No. 09/698,454 filed Oct. 27, 2000, which claims the benefit of U.S. Provisional Applications 60/201,494 filed on May 3, 2000, and 60/163,906 filed on Nov. 5, 1999, the entire disclosures of which are incorporated by reference herein.

FIELD OF THE INVENTION

This invention relates to compositions containing non-denatured soy products, or soy trypsin inhibitors, and optionally additional anti-cancer or cosmetically active agents. These compositions can be applied topically to reduce the risk of UV-induced cutaneous tumors.

BACKGROUND OF THE INVENTION

Skin, the largest organ of the human body, is continuously exposed to environmental insults such as smoke, pollution, and ultraviolet (UV) irradiation. The thinning of the ozone layer, which is expected to progress for at least several decades, reduces a major barrier to the passage of ultraviolet-B radiation (UVB) through the atmosphere. UVB, that is, light whose wavelength is in the range between about 280 and about 320 nm, is the main cause of sunburn, tanning, aging of the skin, and skin cancer.

The non-melanoma skin cancers (NMSC), including basal-cell and squamous-cell carcinoma, are the most common types of cancer among Caucasian populations. The incidence of NMSC has increased worldwide over the last few decades. Increased recreational and occupational sunlight exposure is commonly regarded as one of the reasons for the higher incidence of cutaneous cancers. The increase in UVB exposure associated with the thinning of the ozone layer is another significant factor. Mortality from NMSC is low, but the estimated recurrence rate of about 50% after five years and the local invasiveness of this type of cancer result in high medical costs. Therefore, NMSC constitutes a substantial public health concern. (Reviewed in Holick and Kligman, editors: Biologic effects of light. Walter de Gruyter, Berlin and New York, 1992).

Photo-carcinogenesis results from a complex interplay of simultaneous and sequential biochemical events. These events, initiated by irradiation of an organism with UV light of an appropriate wavelength, include the formation of DNA photo-products, inaccuracies in DNA repair, mutation of proto-oncogenes and tumor suppressor genes, and UV-induced production of radical species which produce subsequent effects on existing mutations and independently induce further mutations. In addition, other epigenetic events such as immunological responses, antioxidant defenses, and dietary factors may influence the course of carcinogenesis. (Black, H. S., deGruijl, F. R., Forbes P. D., Cleaver, J. E., Ananthaswamy, H. N., deFabo, E. C., Ullrich, S. E., Tyrrell, R. M., Photocarcinogenesis: an overview. J. Photochem. Photobiol. B 40:1, 29-47, August, 1997).

The skin possesses an elaborate antioxidant defense system to deal with UV-induced oxidative stress. Excessive exposure to UV radiation, however, can overwhelm the cutaneous antioxidant capacity, leading to oxidative damage and ultimately to skin cancer and premature skin aging. Therefore, one strategy for photoprotection is to support the endogenous antioxidant system by induction or transdermal delivery of antioxidant enzymes or nonenzymatic antioxidants. Antioxidants such as glutathione, alpha-tocopherol, ascorbate and beta-carotene have been found to be very effective in photoprotection. Components of the antioxidant pathway have also been identified and applied to the skin of patients. Although skin treatments with single components of the antioxidant system such as vitamin E were successful against a wide variety of types of photodamage, they were not shown to affect the progression of UV-induced tumors. The most promising results were obtained in studies combining several compounds, which often resulted in synergy between the protective effects. (Steenvoorden D. D., van Henegouwen G. M., The use of endogenous antioxidants to improve photoprotection, J. Photochem. Photobiol., B 41:1-2, 1-10, November, 1997).

Epidemiological studies suggest that components of vegetables, particularly legumes, are beneficial in lowering the incidence rates of many types of cancer. For example, the rates of breast, colon and prostate cancer are significantly lower among the inhabitants of most countries of the Pacific Basin, but offspring of Pacific Basin natives who have migrated to the United States develop the common Western cancers at approximately the same rate as native Westerners. Such epidemiological studies suggest that dietary and other environmental factors, rather than genetic differences, contribute more significantly to the risk of susceptibility to these cancers. The high consumption of soybean products in Pacific Basin countries, such as Japan, implicates diet as one factor contributing to the relatively extremely low rates of cancer mortality in these countries. (E.g., Wu et al., Soy intake and risk of breast cancer in Asians and Asian Americans. Am. J. Clin. Nutr. 68: 6 Suppl., 1437S-1443S, December, 1998).

Soybeans are a rich source of isoflavones, which possess weak estrogenic activity. Genistein, the main soybean isoflavone, is a specific inhibitor of protein tyrosine kinases and of other enzymes involved in signal transduction. Genistein has been shown to suppress the growth of numerous cancer cells in vitro, and to protect animals in experimental carcinogenesis models from developing both hormone- and non-hormone related cancers. (Reviewed in A. R. Kennedy, Chemopreventive agents: Protease inhibitors, Pharmacology Theories 78 (3), 167-209), 1998 and in Messina et al., Soy intake and cancer risks: A review of the in vitro and in vivo data, Nutrition and Cancer 21 (2), 113-131, 1994).

Soybeans also contain a number of protease inhibitors such as BBI and STI. It is important to note that soy foods do not contain high concentrations of active STI and BBI, because these protease inhibitors block the action of trypsin and other enzymes needed for protein digestion. Although STI is denatured by cooking, heat alone does not inactivate BBI, and consumption of soy products containing high levels of these protease inhibitors leads to serious digestive problems, chronic deficiency in amino acid uptake, and cancer. Indeed, the Chinese did not serve soybeans as food until fermentation techniques were developed to destroy the anti-digestive properties of the soy foods (2nd century B.C.E.). During the production of soy foods today, pureed soybeans are soaked in an alkaline solution and then pressure-heated to 115°C in order to denature the protease inhibitors as much as possible.

Limtrakul et al. attempted to identify a safe level of soy proteins for nutritional consumption, which would be beneficial in the prevention of cancer. Skin tumors were chemically induced in mice, which were fed soy protein isolate (SPI)

exclusively, and in mice which were fed SPI supplemented with soymilk proteins (SMP). It was reported that "the percentage of tumor-bearing mice and the volume of tumor tended to be lower in the mice on the SMP diet". *Life Sciences* 1993, 53, 1591-1596. When defatted soybeans are treated first with alkaline, then with acid solution, SPI is the precipitate and SMP is the supernatant. The Limtrakul study shows the potential of soy proteins to affect skin cancer progression, when the proteins are orally consumed. However, it was also emphasized that higher levels of dietary intake of SMP would result in major health problems.

It is clear that a need exists for safe, efficacious and economical agents that prevent or reduce incidence of cancer, particularly for NMSC, which may be simply and conveniently administered. Further, economical and prophylactic compositions and methods for the reduction, prevention or inhibition of the progression of UV-induced cutaneous tumors are highly desirable. Since topical application is very simple and convenient, incorporating compositions that reduce skin cancer incidence into a skin-care product would be extremely advantageous. While sunscreens are known to reduce the damage resulting from UV exposure during the period of their application, there is a need for a skin care product that could also slow the progression of already-initiated photocarcinogenic processes. It is an object of the invention to provide such a product.

SUMMARY OF THE INVENTION

The present invention provides a method of reducing the risk of developing UV-induced tumors of the skin of a mammal by topically applying a skin-care composition, preferably to an individual who has already been exposed to or irradiated with UV light. A method of reducing the growth rate of UV-induced cutaneous tumors by topically applying the skin-care composition is also provided, as is a method of preventing the progression of cancer by the same means.

The skin care composition for use in the methods of the invention is formulated for the topical delivery of a non-denatured soy product (e.g., to a mammal such as a human) and comprises a soy product (e.g., a non-denatured soymilk or soybean powder or soybean trypsin inhibitor) and a vehicle. The composition may optionally comprise other anticancer or cosmetically active agents. Certain skin care compositions appropriate for use in the present invention have been described in U.S. patent application Ser. Nos. 09/110,409, 09/621,565 and 09/698,454, filed Jul. 6, 1998, Jul. 21, 2000 and Oct. 27, 2000, respectively, and in International Application No. WO99/04752. Each of the foregoing patent documents is incorporated herein by reference.

Other features and advantages of the present invention will be apparent to those of skill in the art in light of the following description and claims.

BRIEF DESCRIPTION OF THE DRAWINGS

FIGS. 2A-2C are a series of graphs showing the inhibitory effect of Soymilk on the development of skin tumors in SKH-1 mice previously treated with ultraviolet B light. The inhibitory effects of heat-denatured soymilk vs. non-denatured soymilk are compared.

FIGS. 3A-3C are a series of graphs showing the inhibitory effects caffeine on the development of skin tumors in SKH-1 mice previously treated with ultraviolet B light.

DETAILED DESCRIPTION OF THE PREFERRED EMBODIMENTS

Figure 1C:
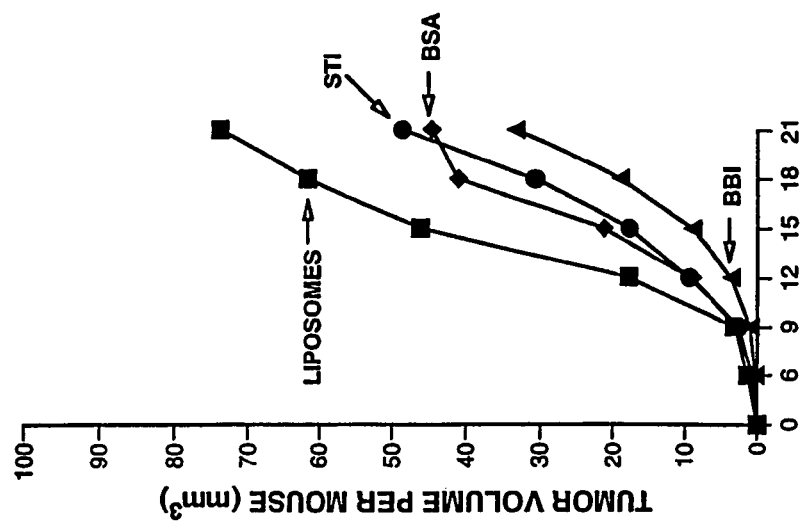
FIGS. 1A-1C are a series of graphs showing the inhibitory effects of STI and BBI on the development of skin tumors in SKH-1 mice previously treated with ultraviolet B light. (BSA—bovine serum albumin; BBI—Bowman-Birk Inhibitor; STI—Soy Bean Trypsin Inhibitor)

It is believed that one skilled in the art can, based upon the description herein, utilize the present invention to its fullest extent. The following specific embodiments are to be construed as merely illustrative and not limitative of the remainder of the disclosure. All publications, patent applications, patents, and other references mentioned herein are incorporated by reference in their entirety.

The present invention is directed to soy-containing compositions and methods of use thereof in the prevention and reduction of the risk of skin cancer. The novel compositions of this invention contain legume products, and preferably soy products, that may be in the form of a fluid (e.g., soymilk) or a solid (e.g., a soybean powder or soymilk powder). What is meant by "soy product" is a substance derived from the soybean, containing the ingredients naturally found in soybeans, at the relative concentrations as found in the beans, excluding water content. In one embodiment, the soy product is a non denatured soy product.

"Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)".

What is meant by "non-denatured soy product" is a soy product in which the processing for the derivation of such soy product (e.g., the temperature, extraction media) did not eliminate its protease inhibitory activity. In one embodiment, the non-denatured state of the soy product of this invention is measured by the presence of an intact soybean trypsin inhibitor (STI) protein.

In another embodiment, the soy product is soymilk. One way to make soymilk is to soak the soybeans in deionized or purified water for several hours, and grind them after they were fully hydrated, with the addition of small quantities of water. (The grinding process allows the soybean milk to be extracted). After collection, the soybean milk may be filtered to remove any residual parts of the bean husk. The soymilk used in this invention can be fresh soymilk as described above, or may be made from soybean powder and water. The soybean powder is milled from soybeans and may also be lyophilized, spray dried, or freeze-dried and the resulting soymilk may or may not be filtered. Soymilk prepared by these methods may have from about 1 to about 90% by weight dry soybean powder. Another example is the use of soymilk powder, made from lyophilized, spray dried or freeze-dried soymilk, with the addition of water and finished with or without filtration or homogenization.

Other methods of soybean extraction could also be used to create the active ingredients used in this invention. In one example, the active ingredients could be extracted from ground soybeans using ethanol/water mixtures, followed by the removal of the ethanol from the extract, in such ways that the protease inhibitory activity of the soybean will be retained.

The compositions of the present invention may contain from about 1% to about 99%, by weight, of the soy product. For example, when a liquid soy product (e.g., soymilk) is used, the composition may contain from about 50% to about 99%, by weight, (e.g., from about 70% to about 99%) of the liquid soy product. For example, when a solid soy product (e.g., soybean powder or soymilk powder) is used, the composition may contain from about 1% to about 50%, by weight (e.g., from about 2% to about 30%, by weight) of the solid soy product. Compositions comprising solid soy products may also comprise water (e.g., distilled water or water contained within soymilk) to form a liquid base for the composition (e.g., to form a cream, lotion, injectable solution or gel). Such compositions may comprise from about 50% to about 98%, by weight (e.g., from about 70% to about 98%, by weight) of water. While not limited to these methods of administration, the compositions of this invention may be delivered topically, orally, or parenterally, although topical administration is preferred.

The soy products useful in this invention may be produced from all soybean species, regardless of their geographic origin, sun exposure, harvest time and the like. However, specific strains, geographic origins or growth conditions might be preferred. These include soybean strains or other legume strains particularly rich in their trypsin inhibitor (e.g. STI, LTI, BBI) content or strains in which, under the proper growth conditions trypsin inhibitor enrichment occurs in the bean. It should be noted that the legume products useful in the compositions of this invention have a distinctive odor, which may be tolerable in some cultures, but is undesired in others. If necessary, the odor of the compositions of this invention can be reduced by using soybean products derived from specific strains of soybeans known to be less odiferous, including, but not limited to, lipoxygenase-2-deficient beans and those having a modified sugar profile, or the like. A process to reduce oxygen levels in the formulation may also reduce the odor. Various masking agents or fragrances may also be used to mask the odor.

In yet another embodiment of the invention, the soy-containing compositions may optionally comprise additional synthetic or natural anti-cancer agents. Examples of such agents include, without limitation, caffeine, Milk Thistle extract, green tea extract, epigallocathechin gallate, silymarins, glucocorticoids and 5-fluorouracil.

A preferred embodiment of the invention comprises the administration of soymilk containing compositions before or after the initiation of UV-induced skin cancer. Especially preferred are embodiments in which the soymilk is not denatured, leaving STI and BBI intact. Soymilk also contains genistein and other isoflavones, and anti-oxidants such as the gamma form of vitamin E, which is essential to the health of the skin. While not wishing to be held to any particular theory, it is hypothesized that these different active components also participate in the prevention of tumor progression. Soymilk also contains lecithins and other emulsifying molecules that facilitate the transdermal delivery of the active components.

As explained above, the present invention extends to a topical cosmetic or pharmaceutical composition comprising a non-denatured soy product (e.g., a non-denatured soymilk or soybean powder) and a cosmetic or pharmaceutically acceptable vehicle and, optionally, additional anti-cancer or cosmetically active agents. As used herein, "topically applying" means directly laying on or spreading on outer skin, e.g., by use of the hands or an applicator such as a wipe, roller, or spray.

The phrase "cosmetic or pharmaceutically acceptable" refers to entities and compositions that are physiologically tolerable and do not typically produce an allergic or similar untoward reaction when administered to a human. As used herein, "cosmetically acceptable" means that the ingredients which the term describes are suitable for use in contact with tissues (e.g., the skin) without undue toxicity, incompatibility, instability, irritation, allergic response, and the like.

The term "vehicle" refers to a diluent, adjuvant, excipient, or carrier. Such cosmetic or pharmaceutical vehicles can be liquids, such as water and oils, including those of petroleum, animal, vegetable or synthetic origin, such as peanut oil, soybean oil, mineral oil, sesame oil and the like. In the art of formulating skin care compositions, the vehicle is often an oil-in-water or a water-in-oil emulsion. Suitable pharmaceutical carriers are described in "Remington's Pharmaceutical Sciences" by E. W. Martin. Suitable cosmetic carriers are described below.

The compositions for use in the methods of the present invention include formulations suitable for topical application to skin. In one embodiment, the composition comprises a non-denatured soy product and a cosmetically acceptable topical carrier. In one embodiment, the cosmetically acceptable topical carrier is from about 50% to about 99.99%, by weight, of the composition (e.g., from about 80% to about 99%, by weight, of the composition).

The compositions may be made into a wide variety of product types that include, but are not limited to, solutions, lotions, creams, gels, sticks, sprays, ointments, cleansing liquid washes, solid bars, shampoos, pastes, foams, powders, mousses, shaving creams, wipes, patches, nail lacquers, wound dressing, adhesive bandages, hydrogels, and films. Make-up, such as foundations, mascaras, and lipsticks also form suitable compositions. These product types may comprise several types of cosmetically acceptable topical carriers including, but not limited to solutions, emulsions (e.g., microemulsions and nanoemulsions), gels, solids and liposomes. Certain non-limitative examples of such carriers are set forth hereinbelow. Other suitable carriers may be formulated by those of ordinary skill in the art.

Topical compositions useful in the subject invention may be formulated as a solution comprising an emollient. Such compositions preferably contain from about 1% to about 50% of an emollient(s). As used herein, the term "emollient" refers to materials used for the prevention or relief of dryness, as well as for the protection of the skin. A wide variety of suitable emollients is known and may be used in the present invention. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present invention may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well known in the cosmetic art and are useful in the present invention. Multiphase emulsion compositions, for example the water-in-oil-in-water type, as disclosed in U.S. Pat. Nos. 4,254,105 and 4,960,764, may also be useful in the present invention. In general, such single or multiphase emulsions contain water, emollients, and emulsifiers as essential ingredients.

The topical compositions of this invention can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

The topical compositions of the present invention can also be formulated as a solid formulation (e.g., a wax-based stick, soap bar composition, powder, or a wipe containing powder).

Liposomal formulations are also useful compositions of the subject invention. In one embodiment, the soymilk or soybean powder particles or soy proteins such as STI are contained within the liposome. Examples of liposomes are unilamellar, multilamellar, and paucilamellar liposomes, which may or may not contain phospholipids. Such compositions can be prepared by first combining the non-denatured soy milk product or the STI with a phospholipid, such as dipalmitoylphosphatidyl choline, cholesterol and water. An example of a method for producing liposomes is described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473-474. Those of skill in the art may make suitable modifications of the method described therein.

Epidermal lipids of suitable composition for forming liposomes may be substituted for the phospholipid. The liposome preparation may then be incorporated into one of the above carriers (e.g., a gel or an oil-in-water emulsion) in order to produce the liposomal formulation. Other compositions and uses of topically applied liposomes are described in Mezei, M., "Liposomes as a Skin Drug Delivery System", Topics in Pharmaceutical Sciences (D. Breimer and P. Speiser, eds.), Elsevier Science Publishers B. V., New York, N.Y., 1985, pp. 345-358, PCT Patent Application No. WO96/31194, Niemiec, et al., 12 Pharm. Res. 1184-88 (1995), and U.S. Pat. No. 5,260,065.

In one embodiment, the liposome is nonionic. In one example, the liposome contains (a) glycerol dilaurate; (b) compounds having the steroid backbone found in cholesterol; and (c) fatty acid ethers having from about 12 to about 18 carbon atoms. In a further embodiment, the liposome comprises glycerol dilaurate, cholesterol, polyoxyethylene-10-stearyl ether, and polyoxyethylene-9-lauryl ether. In one embodiment, these ingredients are in a ratio of about 38:12:33:17.

In one embodiment, the liposomes are present in the topical composition in an amount, based upon the total volume of the composition, of from about 5 mg/ml to about 100 mg/ml such as from about 10 mg/ml to about 50 mg/ml.

The topical compositions useful in the subject invention may contain, in addition to the aforementioned components, a wide variety of additional oil-soluble materials and/or water-soluble materials conventionally used in compositions for use on skin, hair, and nails at their art-established levels.

In addition to such agents, other emollients and surface active agents can be incorporated in the emulsions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerine, sorbitol and the like.

The pharmaceutical or cosmetic composition may be optionally combined with other ingredients such as moisturizers, cosmetic adjuvants, anti-oxidants, depigmenting agents, darkening agents, anti-aging agents, hair removal agents, hair styling agents, nail styling agents, sunscreens, surfactants, bleaching agents, foaming agents, conditioners, humectants, fragrances, colorants, viscosifiers, buffering agents, preservatives, and the like and mixtures thereof. Skincare compositions including these components should be formulated so as not to affect the soy product or soy trypsin inhibitory activity.

Examples of humectants include glycerol, sorbitol, propylene glycol, ethylene glycol, 1,3-butylene glycol, polypropylene glycol, xylitol, malitol, lactitol, allantoin, acetamine MEA, oat protein, hyaluronic acid, and the like. They may be used either singly or in combination.

Because the compositions of this invention are non-denatured, i.e., compositions in which the protease inhibitory activity is retained, they may be more favorable as a medium for microbial growth. Preservatives are useful for substantially preventing microbial decomposition. Examples of preservatives include phenoxyethanol and parabens such as methyl-paraben, ethyl-paraben, and propyl-paraben; salicylic acid, chlorhexidine hydrochloride, phenoxyethanol, sodium benzoate, methyl para-hydroxybenzoate, ethyl para-hydroxybenzoate, propyl para-hydroxybenzoate, butyl para-hydroxybenzoate, isothiazolones and the like. Other examples of preservatives are listed on pages 1654-55 of the International Cosmetic Ingredient Dictionary and Handbook, eds. Wenninger and McEwen (CTFA, $7^{th}$ ed., 1997), hereinafter referred to as the "Cosmetic Handbook." The composition may comprise from about 0.01% to about 20%, by weight (more preferably, from about 0.5% to about 5%, by weight) of preservative. Microbial contamination can also be eliminated by gamma irradiation or microfiltration, or by brief heat treatments that do not result in the elimination of protease inhibitory activity.

Examples of fragrances and odor masks include menthol, anethole, carvone, eugenol, limonene, ocimene, n-decylalcohol, citronellol, a-terpineol, methyl salicylate, methyl acetate, citronellyl acetate, cineole, linalool, ethyl linalool, vanillin, thymol, spearmint oil, peppermint oil, lemon oil, orange oil, sage oil, rosemary oil, cinnamon oil, pimento oil, cinnamon leaf oil, perilla oil, wintergreen oil, clove oil, eucalyptus oil and the like.

Examples of surface active agents include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium α-olefin sulfonate and sodium dioctylsulfosuccinate; N-alkylaminoglycerols, e.g., N-lauryldiaminoethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic™ type surface active agent, and polyoxyethylenesorbitan aliphatic acid esters such as polyoxyethylenesorbitan monooleate and polyoxyethylenesorbitan monolaurate.

Examples of the binder or thickener include cellulose derivatives such as alkali metal salts of carboxymethylcellulose, methyl cellulose, hydroxyethyl cellulose and sodium carboxymethylhydroxyethyl cellulose, alkali metal alginates such as sodium alginate, propylene glycol alginate, gums such as carrageenan, xanthan gum, tragacanth gum, caraya gum and gum arabic, and synthetic binders such as polyvinyl alcohol, polysodium acrylate and polyvinyl pyrrolidone. Thickening agents that can be added to the compositions of this invention to alter viscosity include other polymers such as polyacrylates (e.g., polyacrylamide). Other examples of viscosity modifying agents are listed on pages 1692-97 of the Cosmetic Handbook. To achieve the appropriate viscosity, compositions of the present invention may comprise from about 0.01% to about 20%, by weight (e.g., from about 0.1% to about 5%, by weight) of a thickening agent.

Coloring agents and fragrances also are commonly included in such compositions.

In one embodiment, the topical composition further comprises another cosmetically active agent in addition to the non-denatured soy product. A "cosmetically active agent" is a compound (e.g., a synthetic compound or a compound isolated from a natural source or a natural extract) that has a cosmetic or therapeutic effect on the skin, hair, or nails, including, but not limiting to, lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

The compositions of this invention may be applied prior to, concurrently with or after other active ingredients or compositions to enhance their effect.

Antioxidants and/or chelating agents may also be used to increase shelf life and stability of the compositions. Antioxidants may be added both for formulation stabilization and for biological efficacy. Antioxidant compounds and their derivatives include, but are not limited to, water-soluble antioxidants such as sulfhydryl compounds and their derivatives (e.g., sodium metabisulfite and N-acetyl-cysteine), lipoic acid and dihydrolipoic acid, resveratrol, acetyl-cysteine (Iniferine®) or lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis, and legume extracts. Other examples of antioxidants may be found on pages 1612-13 of the Cosmetic Handbook. The compositions of the present invention may comprises the antioxidant in an amount of from about 0.001% to about 20%, by weight (e.g., from about 0.01% to about 10% by weight) of the composition.

It is preferable to have at least one oil-soluble antioxidant in the compositions of this invention. The antioxidants should be utilized in a stabilizing effective amount and may range in total from about 0.001 to 10% based on the weight of the total composition, preferably from about 0.005 to about 5%. The oil-soluble antioxidants which are useful in the compositions of the present invention include butylated hydroxytoluene (BHT), ascorbyl palmitate, butylated hydroxanisole (BHA), phenyl-α-naphthylamine, hydroquinone, propyl gallate, nordihydroguiaretic acid, and mixtures thereof as well as any other known oil-soluble antioxidant compatible with the other components of the compositions.

Preferably, a water-soluble antioxidant should also be present in the water phase of the compositions of this invention. The water-soluble antioxidants which are useful in the compositions of this invention include ascorbic acid, sodium metabisulfite, sodium bisulfite, sodium thiosulfite, sodium formaldehyde sulfoxylate, isoascorbic acid, thioglyerol, thiosorbitol, thiourea, thioglycolic acid, cysteine hydrochloride, 1,4-diazobicyclo-(2,2,2)-octane and mixtures thereof as well as any other known water-soluble antioxidant compatible with the other components of the compositions.

Chelating agents are also useful in assisting the stabilization of the compositions of this invention. Examples of chelating agents include EDTA and derivatives thereof (e.g., disodium EDTA and dipotassium EDTA), Iniferine®, lactoferrin, and citric acid. Other examples of chelating agents are listed on page 1626 of the Cosmetic Handbook. The compositions of the present invention may comprise the chelating agent in an amount of from about 0.001% to about 20%, by weight (e.g., from about 0.01% to about 10% by weight) of the composition.

Other active ingredients such as sunscreen materials may be utilized in the compositions of the present invention provided that they are physically and chemically compatible with the other components of the compositions. Sunscreens may include organic or inorganic sunscreens, such as methoxyoctylcinnamate and other cinnamate compounds, titanium dioxide and zinc oxide and the like.

Various irritancy mitigants may be added to the compositions of this invention. Irritancy mitigants such as α-bisabolol, panthenol, allantoin, ginkgo biloba, stearoyl glycerrhetinic acid (licorice extract), tea tree oil, butchers' broom, calendula, ginseng and the like may be added.

Other ingredients may include agents that assist in protecting the skin from aging, such as sunscreens, anti-oxidant vitamins such as ascorbic acid, vitamin B, biotin, pantothenic acid, vitamin D, vitamin E and vitamin C, and sodium bisulfite. Yeast extract, gingko biloba, bisabolol, panthenol, alpha hydroxy acids and oligosaccharides such as melibiose are among other ingredients which assist in preventing aging of the skin by such means as irritation mitigation, oxidation mitigation, healing, affecting retinoid metabolism and inhibiting the production of elastase.

The compositions of this invention may also contain other depigmenting agents in addition to the soy product. What is meant by depigmentation is the lightening of the color of an area of skin, including but not limited to, the global lightening of the user's skin tone/complexion (e.g., the face, hands, or whole body, which is uneven as a result of aging skin, or darker than desired because of ethnicity or pathology, and the like), the evening of skin color tone, or the specific lightening of age spots, freckles, or darker pigmented areas such as, but not limited to, post-inflammatory hyper-pigmentary lesions.

Examples of such depigmenting agents include, but are not limited to, lipoic acid, dihydrolipoic acid, resveratrol, ascorbic acid, kojic acid, hydroquinone, isoflavones, retinoids (e.g., retinol, retinoic acid, and retinyl palmitate), tyrosinase inhibitors, melanosome transfer inhibitors, and selective cytotoxic agents for melanocytes, or natural extracts, e.g., licorice extract, gatuline A (pilewort extract), and micromerol (butylene glycol and apple extract), providing these activities. The amount of the depigmenting agent used will depend on the activity of the compound, and will typically range from about 0.001% to about 20%, by weight (e.g., from about 0.01% to about 10%, by weight) of the composition.

Other skin color evening ingredients, such as skin darkening or sunless tanning agents, may also be effective in the skin care compositions for use in this invention.

The composition of the present invention may also contain compounds that enhance the feel of the composition on the skin of the user. Examples of such compounds include, but are not limited to, oils, silicones (e.g., siloxane polymers such as dimethicone) and skin-conditioning agents such as emollients, and humectants. Examples of such skin conditioning agents may be found of pages 1656-1670 of the Cosmetic Handbook.

Compositions which assist in the reduction of lines and wrinkles may also be added to the compositions of this invention. For example, alpha hydroxy acids, hyaluronic acid, Gatuline R (fagus silvitica extract), pigments and scattering aids such as zinc oxide and titanium dioxide may be used in the compositions of this invention in this capacity.

Anti-inflammatory agents may also be used in the compositions of this invention. Not only should these agents assist in mitigating irritation, they may assist in treating wrinkles and lines in the skin. Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxycorticosterone acetate, dexamethoasone, dichlorisone, deflorasonediacetate, diflucortolone valerate, fluadronolone, fluclarolone acetonide, fludrocortisone, flumethasone pivalate, fluosinolone acetonide, fluocionide, flucortine butylester, fluocortolone, flupredidene (flupredylidene) acetate, flurandronolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and its esters, chlorprednisone acetate, clocortelone, clescinolone, dichlorisone, diflupredmate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone and mixtures thereof may be used. Preferably, hydrocortisone or natural extracts with similar activity may be used.

Nonsteroidal anti-inflammatory agents may also be employed in the compositions of this invention, such as salicylates, acetic acid derivatives, fenamates, propionic acid derivatives and pyrazoles or mixtures thereof. Other synthetic and natural anti-inflammatory agents may also be used.

Additional active ingredients having topical activity may be utilized in the compositions of this invention. Azole-type anti-fungal and anti-bacterial agents may be employed in the compositions of this invention in their base form. For example, ketoconazole, miconazole, itraconazole, elubiol, and like related imidazole antifungals and antibacterials are useful in the topical formulations of this invention.

It can be readily appreciated that a transdermal route of administration may be enhanced by use of a dermal penetration enhancer, e.g., such as enhancers described in U.S. Pat. No. 5,164,189, U.S. Pat. No. 5,008,110, and U.S. Pat. No. 4,879,119, issued Nov. 7, 1989 to Aruga et al. In one embodiment, a composition of the present invention can be delivered in a controlled release system, such as using a transdermal patch, liposomes, or other modes of administration. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)].

In another embodiment, a controlled release system can be placed in proximity of the target tissues of the mammal, thus requiring only a fraction of the systemic dose [see, e.g., Goodson, in Medical Applications of Controlled Release, supra, vol. 2, pp. 115-138 (1984)]. In particular, a controlled release system can be introduced into an animal in proximity of the site of inappropriate immune activation or a tumor. Other controlled release systems are discussed in a review by Langer [Science 249:1527-1533 (1990)].

In yet another embodiment of the invention, the soybean trypsin inhibitor may be produced by recombinant means. The nucleotide and protein sequences of STI are known. See GenBank Accession No. AF314823. Methods for recombinant expression of STI are well known to those of ordinary skill in the art. In an alternative embodiment, the STI so produced may be modified at the genetic level (e.g. replacing amino acids to change local charges, to enhance skin penetration without compromising activity, or to enhance activity without compromising skin penetration) or chemically post synthesis (e.g. additional lipid or sugar groups) to enhance uptake of the STI into the skin of the patient.

Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis.

Compositions of the present invention may be prepared by mixing the desired ingredients. For example, soymilk is mixed with the chelating agent, preservative, and/or antioxidant. A thickener is then added to the system, and the mixture is further mixed until it reaches homogeneity at the desired viscosity. The compositions of the present invention may be prepared under an argon, nitrogen, or other inert gaseous blanket in order to enhance formulation stability and/or to reduce soybean odor. The compositions of this invention may be packaged in a tube, a sealed packet, a jar, a pump, a bottle, a can, a pledget, a towelet, a wipe or the like. An airtight package such as an aluminum tube, aluminum pocket, pump, laminate tube, or the like, can also be used to further enhance product stability.

The skin-care compositions for use in the methods of this invention may be applied daily for at least four weeks, and more preferably at least eight weeks, by which an effect upon the appearance of skin should be observed. Application may be continued as long as desired to maintain the condition of the skin and to reduce skin cancer risk.

The topically active pharmaceutical or cosmetic composition should be applied in an amount effective to effect the desired changes in the skin. As used herein, "amount effective" shall mean an amount sufficient to cover the region of skin surface where preventing cancer, inhibiting the growth rate of a cutaneous tumor, or reducing the risk of cancer is desired. Preferably, the composition is applied to the skin surface such that, based upon a cm$^2$ of skin surface, from about 2 µl/cm$^2$ to about 500 µl/cm$^2$ of topically active agent is present when preventing cancer, inhibiting the growth rate of a cutaneous tumor, or reducing the risk of cancer is desired.

The following examples are provided to describe the invention in further detail. These examples are provided for illustrative purposes only, and are not to be construed as limiting the invention.

Example 1

Soymilk Reduces UVB-Induced Tumorigenesis

Female SKH-1 mice, 6-7 weeks old, were purchased from Charles River Laboratories (Kingston, N.Y.) and were housed for at least one week before use. Mice were given water and Purina Laboratory Chow 5001 diet (Ralston-Purina, St. Louis, Mo.) ad libitum. Animal care was based on the "Guide for the Care and Use of Laboratory Animals", NIH Publication No. 85-23. Ultraviolet B light (UVB) lamps (FS72T12-UVB-HO) were from National Biological Corp. (Twinsburg, Ohio). Mice were irradiated with UV lamps that emit both UVB (280-320 nm, 75-80% of total energy) and UVA (320-375 nm, 20-25% of total energy). The UVB dose was quantified with a Spectra 305 dosimeter from Daevlin Co. (Byran, Ohio). The radiation was further calibrated with a Research radiometer/photometer model IL1700 from International Light Inc. (Newburgport, Mass.).

Mice were irradiated with UVB light (30 mJ/cm$^2$) for 25 to 30 seconds twice a week for 20 weeks. UVB irradiation was stopped when the first tumor was visible on the back of one mouse. This mouse was removed, and the population was classified as "at high risk for skin tumor development." Three weeks later, mice with no tumors were randomized into groups of 30 mice. One group (the control) was not treated, and other groups were topically treated, once a day, five days a week, with 100 µl of test material. Agents tested in this example included STI and BBI, and either freshly prepared soymilk or freshly prepared soymilk that was heat denatured at 90°C for 20 min. Controls include vehicle alone and an unrelated protein (BSA).

The number of skin tumors and tumor sizes were measured every three weeks, using the methods described in Lou et al., (Effects of oral administration of tea, decaffeinated tea, and caffeine on the formation and growth of tumors in high risk SKH-1 mice previously treated with ultraviolet B light. Nutrition and Cancer 33, p. 146-153, 1999). The results of these measurements are summarized in Table 1 and shown in FIGS. 1A-1C and FIGS. 2A and 2B. An increase in tumor volume per mouse during the 21 weeks of the treatment phase was observed in each treatment regimen. The daily treatment with heated soymilk did not affect the rate of increase in tumor volume per mouse relative to control. Surprisingly, daily treatment with fresh soymilk had a dramatic effect on tumor volume. Tumor growth was significantly slower, and final tumor volumes were reduced by a factor of two to three in the mice treated with fresh soymilk, relative to the untreated or heated soymilk treated mice. See FIG. 2C. Table 1 shows the effect of fresh soymilk on tumor progression as measured by several additional parameters. The percent of tumor-bearing mice was reduced following treatment with fresh soymilk, as were the number of tumors per mouse and the tumor volume per tumor.

Figure 1B:
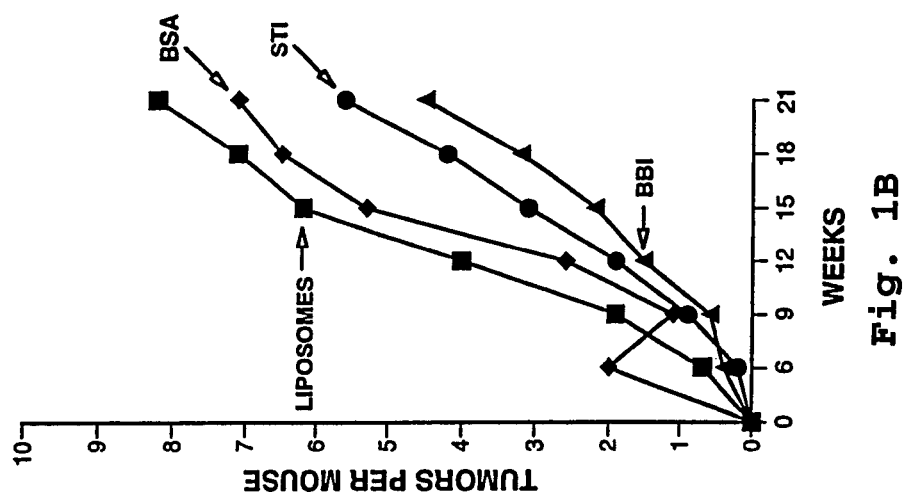
Figure 1A:
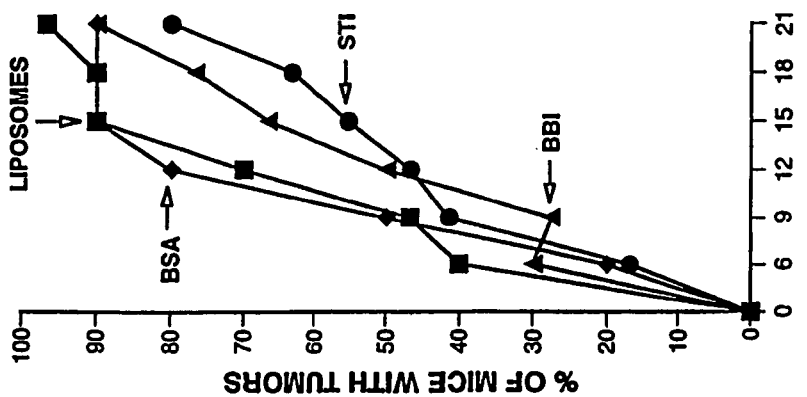
Figure 4A:
FIGS. 4A-4C are three photographs showing the reduction in size and number of UV-induced tumors among mice treated topically with non-denatured soymilk (FIG. 4A) compared to mice treated with heat-denatured soymilk (FIG. 4B) or water (FIG. 4C).
Figure 4B:
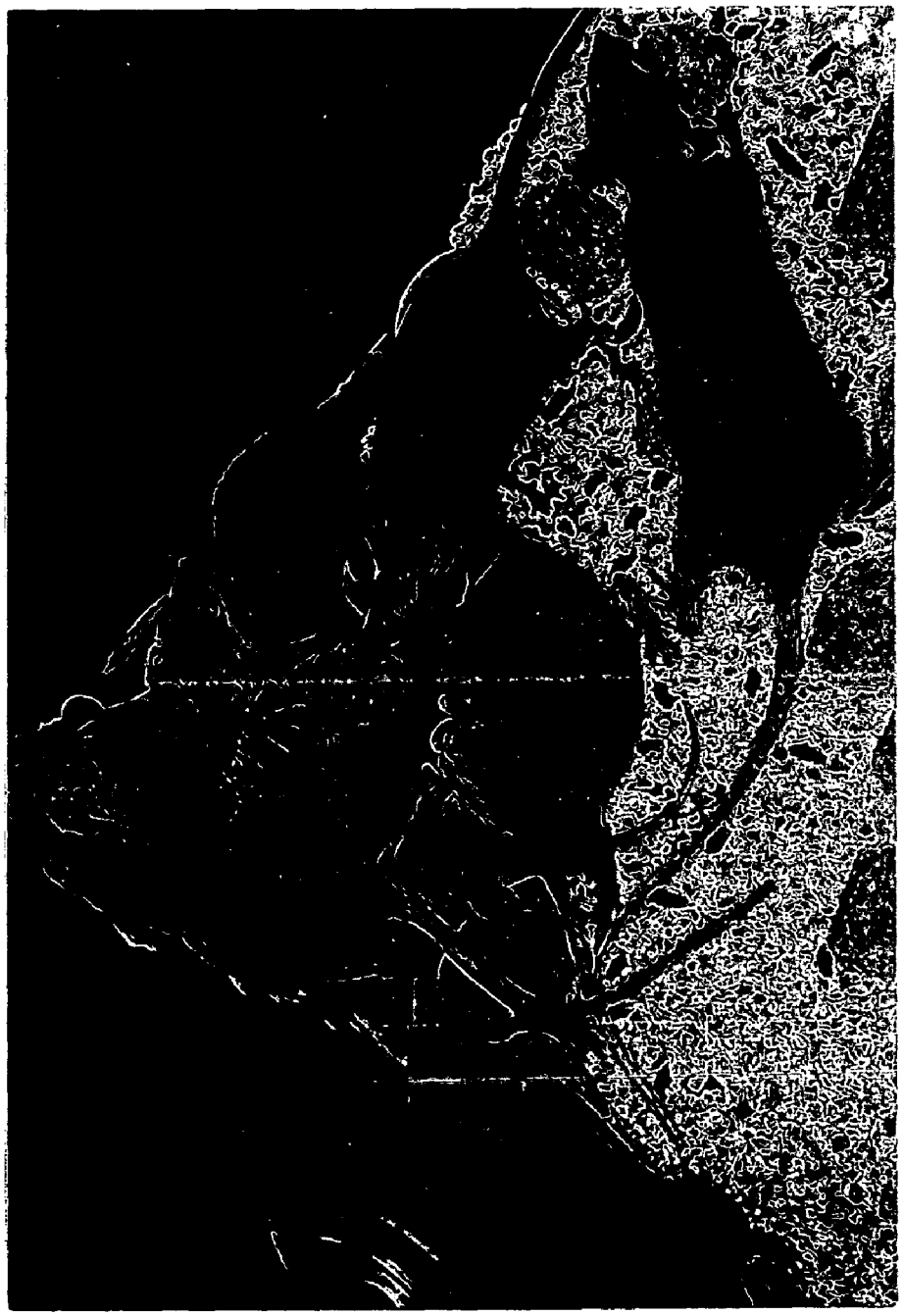
Figure 4C:

FIGS. 1A-1C show the effects of treatment of BBI and STI on mice irradiated with UVB. Surprisingly, using STI alone had an unexpected and significant effect on tumor progression. See FIGS. 1A-1C. The dramatic difference in results produced by treatment with fresh soymilk versus heat denatured soymilk, see FIGS. 2A-2C, also points to STI as an active anti-tumor ingredient, since it is well known that STI is denatured by cooking, but heat alone will not denature BBI, nor does it affect phytoestrogens. FIGS. 4A-4C are three photographs showing a random group of mice from each treatment group. This figure clearly demonstrates the reduced tumorigenicity in the mice treated with fresh soymilk vs heated treated soymilk or water. Compare FIG. 4A with 4B or 4C. These data indicate that topical treatment with fresh soymilk reduces UVB-induced tumor growth and progression in a high risk, pre-exposed population. These data also suggest that some of the active(s) of fresh soymilk that are involved in the tumor growth reduction are heat sensitive.

TABLE I

Effects of Topical Applications of Soymilk, STI, BBI, and Caffeine on the Development of Skin Tumors in SKH-1 Mice Previously Treated with Ultraviolet B Light

| Week | Treatment | Number of mouse per group | Weight per mouse (g) | Percent of mice with tumors | Tumors per mouse | Tumor volume per tumor ($mm^3$) | Tumor volume per mouse ($mm^3$) |
|---|---|---|---|---|---|---|---|
| 0 | No treatment | 30/30 | 29.9 ± 0.5 | 0 | 0 | 0 | 0 |
|  | Water | 29/29 | 30.0 ± 0.3 | 0 | 0 | 0 | 0 |
|  | Soymilk | 30/30 | 29.9 ± 0.5 | 0 | 0 | 0 | 0 |
|  | Heated Soymilk | 30/30 | 30.0 ± 0.5 | 0 | 0 | 0 | 0 |
|  | Liposomes | 30/30 | 30.0 ± 0.4 | 0 | 0 | 0 | 0 |
|  | STI | 30/30 | 30.2 ± 0.4 | 0 | 0 | 0 | 0 |
|  | BBI | 30/30 | 30.1 ± 0.4 | 0 | 0 | 0 | 0 |
|  | BSA in liposomes | 30/30 | 30.1 ± 0.2 | 0 | 0 | 0 | 0 |
|  | Acetone | 30/30 | 30.1 ± 0.2 | 0 | 0 | 0 | 0 |
|  | Caffeine (1.2 mg) | 30/30 | 30.0 ± 0.2 | 0 | 0 | 0 | 0 |
| 6 | No treatment | 30/30 | 30.3 ± 0.4 | 47.7% | 0.7 ± 0.2 | 1.5 ± 0.7 | 1.1 ± 0.5 |
|  | Water | 29/29 | 30.4 ± 0.5 | 27.6% | 0.4 ± 0.2 | 0.5 ± 0.0 | 0.2 ± 0.1 |
|  | Soymilk | 30/30 | 29.9 ± 0.4 | 6.7% | 0.1 ± 0.0 | 0.5 ± 0.0 | 0 |
|  | Heated Soymilk | 30/30 | 30.4 ± 0.6 | 36.7% | 0.4 ± 0.1 | 1.1 ± 0.4 | 0.5 ± 0.2 |
|  | Liposomes | 30/30 | 30.0 ± 0.4 | 40.0% | 0.7 ± 0.2 | 2.0 ± 0.7 | 1.4 ± 0.6 |
|  | STI | 30/30 | 29.7 ± 0.5 | 16.7% | 0.2 ± 0.1 | 3.5 ± 1.9 | 0.8 ± 0.6 |
|  | BBI | 30/30 | 30.0 ± 0.5 | 30.0% | 0.4 ± 0.1 | 0.9 ± 0.3 | 0.3 ± 0.1 |
|  | BSA in liposomes | 30/30 | 30.3 ± 0.4 | 20.0% | 2.0 ± 0.1 | 2.5 ± 1.9 | 0.6 ± 0.5 |
|  | Acetone | 30/30 | 29.6 ± 0.4 | 36.7% | 0.7 ± 0.2 | 2.6 ± 0.9 | 1.9 ± 0.8 |
|  |  | 30/30 | 29.3 ± 0.4 | 16.7% | 0.2 ± 0.1 | 1.3 ± 0.7 | 0.2 ± 0.1 |
| 9 | No treatment | 30/30 | 30.5 ± 0.3 | 43.3% | 0.8 ± 0.2 | 3.3 ± 1.5 | 2.7 ± 1.3 |
|  | Water | 29/29 | 30.6 ± 0.5 | 48.3% | 1.0 ± 0.3 | 1.3 ± 0.3 | 1.3 ± 0.6 |
|  | Soymilk | 30/30 | 30.1 ± 0.4 | 20.0% | 0.2 ± 0.1 | 0.5 ± 0.0 | 0.1 ± 0.0 |
|  | Heated Soymilk | 30/30 | 30.3 ± 0.5 | 46.7% | 0.7 ± 0.1 | 4.8 ± 1.9 | 3.2 ± 1.3 |
|  | Liposomes | 30/30 | 30.2 ± 0.4 | 46.7% | 1.9 ± 0.5 | 1.7 ± 0.6 | 3.2 ± 1.2 |
|  | STI | 29/30 | 30.0 ± 0.4 | 41.4% | 0.9 ± 0.2 | 3.0 ± 1.4 | 2.6 ± 1.4 |
|  | BBI | 30/30 | 29.9 ± 0.5 | 27.6% | 0.6 ± 0.2 | 1.7 ± 0.8 | 1.0 ± 0.7 |
|  | BSA in liposomes | 30/30 | 30.5 ± 0.4 | 50.0% | 1.1 ± 0.3 | 2.7 ± 1.2 | 2.9 ± 1.4 |
|  | Acetone | 30/30 | 30.4 ± 0.5 | 60.0% | 1.4 ± 0.5 | 2.8 ± 0.9 | 4.0 ± 1.5 |
|  | Caffeine (1.2 mg) | 30/30 | 29.4 ± 0.4 | 13.3% | 0.2 ± 0.1 | 3.4 ± 2.2 | 0.7 ± 0.5 |
| 12 | No treatment | 30/30 | 30.4 ± 0.4 | 70.0% | 1.9 ± 0.3 | 2.8 ± 0.7 | 5.4 ± 1.7 |
|  | Water | 29/29 | 31.1 ± 0.5 | 58.6% | 1.9 ± 0.5 | 2.3 ± 0.5 | 4.4 ± 1.2 |
|  | Soymilk | 30/30 | 30.4 ± 0.4 | 40.0% | 0.7 ± 0.2 | 1.8 ± 0.4 | 1.2 ± 0.4 |
|  | Heated Soymilk | 30/30 | 30.2 ± 0.6 | 53.3% | 1.0 ± 0.2 | 14.4 ± 6.0 | 14.9 ± 6.3 |
|  | Liposomes | 30/30 | 30.0 ± 0.4 | 70.0% | 4.0 ± 0.9 | 4.4 ± 1.0 | 17.8 ± 5.2 |
|  | STI | 29/30 | 29.8 ± 0.5 | 46.7% | 1.9 ± 0.5 | 4.8 ± 1.3 | 9.4 ± 3.9 |
|  | BBI | 30/30 | 30.6 ± 0.5 | 50.0% | 1.5 ± 0.4 | 2.4 ± 0.8 | 3.7 ± 1.8 |
|  | BSA in liposomes | 30/30 | 30.4 ± 0.5 | 80.0% | 2.6 ± 0.6 | 3.5 ± 1.0 | 9.1 ± 3.1 |
|  | Acetone | 30/30 | 30.0 ± 0.4 | 80.0% | 4.5 ± 0.9 | 5.2 ± 1.0 | 23.4 ± 7.1 |
|  | Caffeine | 30/30 | 29.0 ± 0.3 | 50.0% | 1.3 ± 0.4 | 3.2 ± 0.8 | 4.0 ± 1.9 |
| 15 | No treatment | 30/30 | 30.6 ± 0.4 | 76.7% | 2.9 ± 0.5 | 5.8 ± 1.4 | 16.8 ± 5.7 |
|  | Water | 29/29 | 31.2 ± 0.4 | 82.8% | 3.5 ± 0.6 | 2.8 ± 0.6 | 9.7 ± 3.4 |
|  | Soymilk | 30/30 | 30.7 ± 0.3 | 46.7% | 1.1 ± 0.3 | 3.0 ± 0.8 | 3.4 ± 1.0 |
|  | Heated Soymilk | 30/30 | 30.6 ± 0.5 | 70.0% | 2.3 ± 0.4 | 10.1 ± 3.6 | 22.9 ± 7.9 |
|  | Liposomes | 30/30 | 29.6 ± 0.9 | 90.0% | 6.2 ± 1.1 | 7.5 ± 1.3 | 46.2 ± 13.2 |
|  | STI | 29/30 | 30.1 ± 0.4 | 55.2% | 3.1 ± 0.7 | 5.8 ± 2.1 | 17.8 ± 7.9 |
|  | BBI | 30/30 | 30.6 ± 0.5 | 66.7% | 2.2 ± 0.4 | 4.1 ± 0.8 | 9.0 ± 2.4 |
|  | BSA in liposomes | 30/30 | 30.5 ± 0.4 | 90.0% | 5.3 ± 0.8 | 4.0 ± 0.7 | 21.4 ± 6.6 |
|  | Acetone | 30/30 | 30.0 ± 0.3 | 83.3% | 6.6 ± 1.0 | 7.4 ± 1.3 | 48.3 ± 16.7 |
|  | Caffeine (1.2 mg) | 30/30 | 29.4 ± 0.3 | 56.7% | 2.1 ± 0.5 | 3.2 ± 0.6 | 6.7 ± 2.2 |
| 18 | No treatment | 30/30 | 31.6 ± 0.4 | 83.3% | 4.2 ± 0.6 | 9.0 ± 2.0 | 38.0 ± 12.8 |
|  | Water | 28/29 | 32.0 ± 0.5 | 96.6% | 5.4 ± 0.6 | 4.0 ± 1.3 | 21.5 ± 7.5 |
|  | Soymilk | 30/30 | 30.7 ± 0.4 | 66.7% | 1.9 ± 0.5 | 6.5 ± 1.8 | 12.3 ± 4.6 |
|  | Heated Soymilk | 30/30 | 31.0 ± 0.6 | 83.3% | 4.1 ± 0.7 | 6.9 ± 2.4 | 28.7 ± 9.8 |
|  | Liposomes | 30/30 | 30.9 ± 0.5 | 90.0% | 7.1 ± 1.0 | 8.7 ± 1.1 | 61.7 ± 15.0 |
|  | STI | 28/30 | 30.0 ± 0.4 | 63.3% | 4.2 ± 0.9 | 7.3 ± 2.2 | 30.7 ± 11.9 |
|  | BBI | 30/30 | 30.7 ± 0.5 | 76.7% | 3.2 ± 0.6 | 5.9 ± 1.3 | 19.0 ± 4.6 |
|  | BSA in liposomes | 30/30 | 30.9 ± 0.5 | 90.0% | 6.5 ± 0.9 | 6.3 ± 1.0 | 41.1 ± 9.7 |
|  | Acetone | 29/30 | 30.7 ± 0.5 | 86.7% | 6.9 ± 1.0 | 8.4 ± 1.3 | 57.4 ± 13.7 |
|  | Caffeine | 30/30 | 29.6 ± 0.4 | 80.0% | 3.6 ± 0.6 | 6.2 ± 1.3 | 22.1 ± 6.2 |
| 21 | No treatment | 30/30 | 31.5 ± 0.3 | 100.0% | 5.9 ± 0.7 | 8.8 ± 2.1 | 51.9 ± 16.3 |
|  | Water | 28/29 | 32.0 ± 0.4 | 96.6% | 6.3 ± 0.6 | 6.4 ± 2.4 | 40.6 ± 15.6 |

TABLE I-continued

Effects of Topical Applications of Soymilk, STI, BBI, and Caffeine on the Development of Skin Tumors in SKH-1 Mice Previously Treated with Ultraviolet B Light

| Week | Treatment | Number of mouse per group | Weight per mouse (g) | Percent of mice with tumors | Tumors per mouse | Tumor volume per tumor (mm³) | Tumor volume per mouse (mm³) |
|---|---|---|---|---|---|---|---|
| | Soymilk | 30/30 | 31.1 ± 0.3 | 83.3% | 2.7 ± 0.5 | 4.8 ± 1.3 | 12.9 ± 4.4 |
| | Heated Soymilk | 29/30 | 31.3 ± 0.6 | 90.0% | 6.7 ± 0.9 | 8.9 ± 3.2 | 59.9 ± 20.9 |
| | Liposomes | 30/30 | 30.9 ± 0.4 | 96.7% | 8.2 ± 1.1 | 9.0 ± 1.5 | 73.7 ± 15.0 |
| | STI | 28/30 | 30.6 ± 0.4 | 80.0% | 5.6 ± 0.9 | 8.6 ± 3.2 | 48.7 ± 23.3 |
| | BBI | 30/30 | 30.8 ± 0.4 | 90.0% | 4.5 ± 0.6 | 7.4 ± 2.0 | 33.2 ± 9.6 |
| | BSA in liposomes | 30/30 | 30.7 ± 0.4 | 90.0% | 7.1 ± 0.8 | 6.3 ± 1.0 | 44.7 ± 11.6 |
| | Acetone | 28/30 | 30.5 ± 0.4 | 90.0% | 6.9 ± 0.9 | 9.6 ± 2.0 | 65.7 ± 0.9 |
| | Caffeine | 30/30 | 29.9 ± 0.3 | 76.7% | 4.0 ± 0.7 | 5.3 ± 1.0 | 21.5 ± 6.0 |

SKH-1 mice (7-8 weeks old) were treated with ultraviolet B light (UVB; 30 mJ/cm²) twice weekly for 20 weeks and UVB treatment was stopped. Three weeks later, the mice (with no visible tumors) were randomized into 10 groups (30 mice per group) and the mice were treated topically: group 2, 100 ul water; group 3, 100 ul Soymilk; group 4, 100 ul heated Soymilk; group 5, 100 ul liposomes; group 6, trypsin inhibitor (STI; 0.8 mg; T9003, Sigma) in 100 ul liposomes; group 7, Bowman-Birk protease inhibitor (BBI; 0.8 mg; T97770, Sigma) in 100 ul liposomes; group 8, bovine serum albumin (BSA; 0.8 mg) in 100 ul liposomes; group 9, 100 ul acetone; group 10, caffeine, CAF; 1.2 mg) in 100 ul acetone once a day 5 days per week for 21 weeks.

Example 2

Caffeine Reduces UVB-Induced Tumorigenesis

The experiment described in Example 1 was also performed using a topical caffeine treatment. Caffeine was purchased from Sigma (St. Louis, Mo.). Acetone was from Fisher Scientific (Springfield, N.J.). Mice were treated daily, five days a week with caffeine (1.2 mg) in 100 μl acetone or with 100 μl of acetone only. Experimental procedures and measurements were identical to those described in Example 1, and the two experiments were performed at the same time, using the same UVB-irradiated population.

Figure 5A:
FIGS. 5A and 5B are a pair of photographs showing the reduction in size and number of UV-induced tumors among mice treated topically with a solution of caffeine in acetone (FIG. 5B) compared to mice treated with acetone alone (FIG. 5A).
Figure 5B:
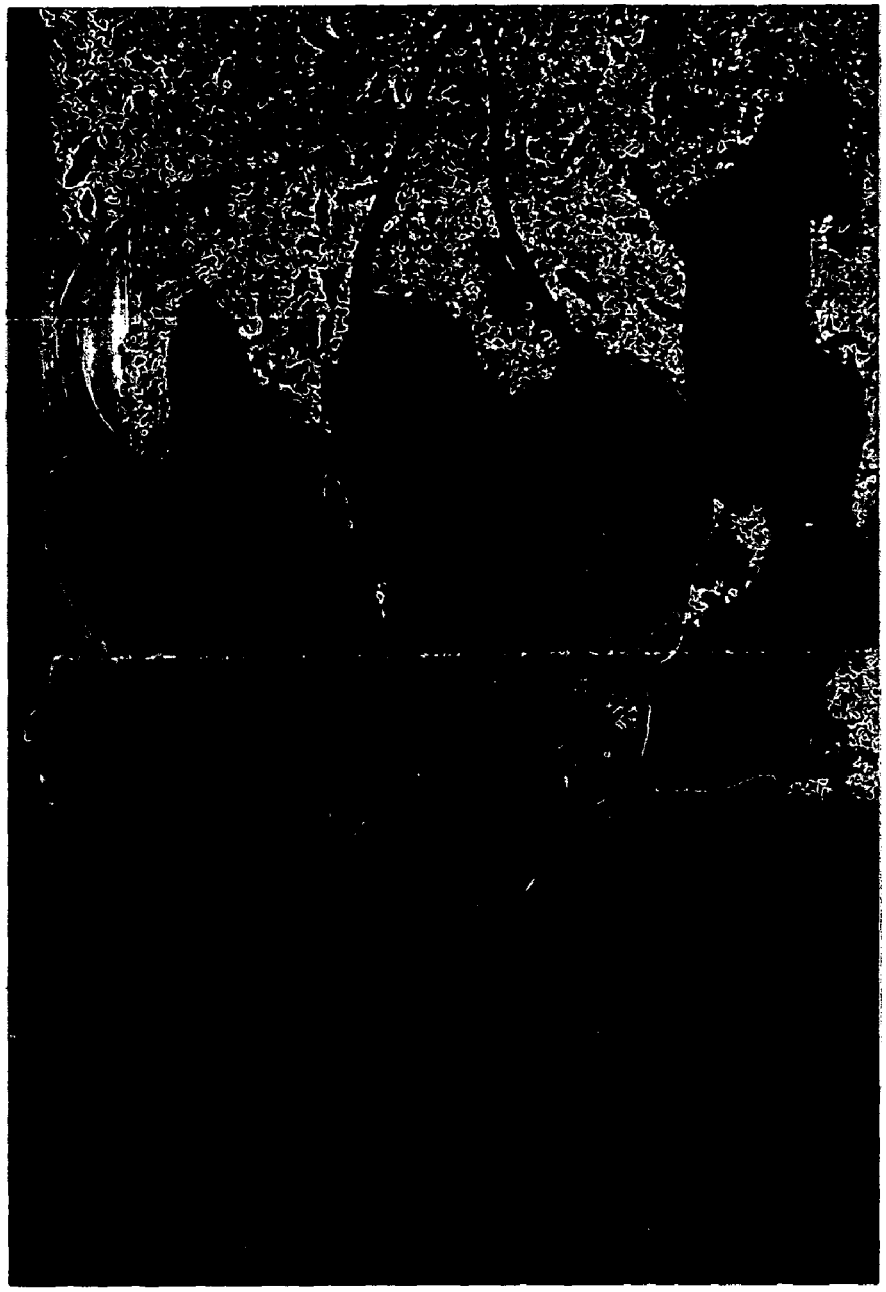

FIGS. 3A-3C show that tumor progression following acetone treatment was very similar to that of the untreated group graphed in FIG. 2. The caffeine treated mice showed a marked delay in tumor progression, as evident from the tumor volume per mouse data in FIG. 3C. The additional parameters reported in Table 1 further support this observation of the beneficial effect of caffeine on tumor progression. The percentage of tumor-bearing mice was reduced following caffeine treatment, as were the number of tumors per mouse and the tumor volume per tumor. FIGS. 5A and 5B are two pictures, each depicting a random group of mice from acetone treated (FIG. 5A) vs. caffeine treated (FIG. 5B mice). This figure clearly demonstrates the reduced tumorigenicity in the caffeine-treated mice.

Example 3

Preparation of Soymilk from Soybean Powder 160 g of soybean powder (Sunlight Foods, Taipei, Taiwan) was added to about 1440 g of deionized water. The mixture was stirred at room temperature for about 1 hour. The mixture was then filtered through a sieve having holes of 75 μm diameter. The filtrate resulted in about 1.1 kg of soymilk.

Example 4

Preparation of Soymilk Gel from Soymilk

The following compositions of this invention were prepared as follows. The weight percentages of each ingredient in the compositions are indicated below in Table 2 and Table 3. First, the soymilk, as prepared in example 3, was placed into a first beaker. The preservative Phenonip® (a mixture of the preservatives methyl-paraben, propyl-paraben, ethyl-paraben, and phenoxy-ethanol sold by NIPA, Wilmington, Del.) or the preservative phenoxyethanol were added to the soymilk. Next, the chelating agent Disodium EDTA and in some examples the humectant glycerin were added to the first beaker and mixed with the soymilk. It is also possible to further add cyclomethicone, or dimethicone (tradename Dow Corning 200 Fluid®), or PolySorbate 20, or Aluminum Starch Octyl Succinate, or Sucrose Cocoate, or PEG-6 Capric/Caprylic Triglycerides to the soymilk mixture at this step as required in some examples in Table 2 and Table 3. A mixture of the thickener polyacrylamide, laureth-7, and C13-14 isoparaffins (sold by Seppic, Paris, France under the Tradename Sepigel®) was added to a second beaker along with the anti-oxidant BHT. The ingredients in the second beaker were then added to the ingredients of the first beaker and mixed until homogenous. The anti-oxidants ascorbic acid, sodium ascorbyl phosphate, lactoferrin, or tocopherol were then added to the beaker and homogeneously mixed to form the resulting gel.

Example 5

Preparation of Soymilk Gel from Soybean Powder, Soymilk Powder or Soybean Extract The following compositions of this invention were prepared as follows. The weight percentage of each ingredient in each of the preparations is indicated below in Table 3. First, the soymilk powder (Devansoy Farms, Carroll, Iowa) or the soybean powder (Sunlight Foods, Taipei, Taiwan) or the Soybean Extract and deionized water were placed into a first beaker and mixed to reconstitute the soy powder. The preservative Phenonip® and the chelating agent Disodium EDTA were then added to the first beaker and mixed with the soymilk. A mixture of polyacrylamide, laureth-7, and C13-14 isoparaffins was added to a second beaker along with the anti-oxidant BHT. The ingredients in the second beaker were then added to the ingredients of the first beaker and mixed until homogenous.

TABLE 2

Soybean Essence formulations

| | 24 | 26 | 27 | 28 | 33 | 34 | 35 |
|---|---|---|---|---|---|---|---|
| Soymilk | 94.40% | 92.40% | 90.70% | 94.70% | | | |
| Phenoxyethanol and Parabens | 1.00% | 1.00% | 1.00% | 1.00% | 1.00% | 1.00% | 1.00% |
| Glycerin | | | 5.00% | | | | |
| Disodium EDTA | 0.05% | 0.05% | 0.05% | 0.05% | 0.05% | 0.05% | 0.05% |
| Polyacrylamide/Laureth-7/$C_{13-14}$ Isoparrafin | 3.50% | 3.50% | 3.20% | 3.20% | 3.20% | 3.20% | 3.20% |
| Ascorbic Acid | | 1.00% | | | | | |
| Butylated Hydroxytoluene | 0.05% | 0.05% | 0.05% | 0.05% | 0.05% | 0.05% | 0.05% |
| Deionized Water | | | | | 90.70% | 90.70% | 85.70% |
| Lactoferrin | 1.00% | 1.00% | | | | | |
| Tocopherol | | 1.00% | | | | | |
| Dow Corning 200 Fluid | | | | 1.00% | | | |
| Soymilk Powder | | | | | 5.00% | | |
| Soybean Extract using Ethanol/Water Mixture | | | | | | 5% | 10% |
| TOTAL | 100% | 100% | 100% | 100% | 100% | 100% | 100% |

TABLE 3

Soybean Essence formulations

| | Soybean Essences | | | | |
|---|---|---|---|---|---|
| | 1 | 6 | 8 | 21 | 23 |
| Soymilk | 87.42% | 89.04% | 96.09% | 96.05% | 95.70% |
| Phenoxyethanol | 0.73% | | | | |
| Phenoxyethanol and Parabens | | 1.00% | 1.00% | 1.00% | 1.00% |
| Glycerin | 2.50% | 2.50% | | | |
| Cyclomethicone | 2.00% | | | | |
| Aluminum Starch Ocetyl Succinate | 0.75% | | | | |
| Sucrose Cocoate | 1.00% | 1.00% | | | |
| PEG-6 Capric/Caprylic Triglycerides | 3.00% | 3.00% | | | |
| Disodium EDTA | 0.10% | 0.10% | | | 0.05% |
| Polyacrylamide/Laureth-7/$C_{13-14}$ Isoparrafin | 2.50% | 2.75% | 2.90% | 2.90% | 3.20% |
| Ascorbic Acid | | 0.01% | | | |
| Butylated Hydroxytoluene | | 0.10% | 0.01% | 0.05% | 0.05% |
| Polysorbate 20 | | 0.50% | | | |
| TOTAL | 100% | 100% | 100% | 100% | 100% |

While certain preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of slowing the progression of a cutaneous tumor comprising topical application of at least one composition containing a non-denatured, soy product in an amount of from about 0.01-99% by weight in a carrier, wherein said non-denatured, soy product comprises a non-denatured, Kunitz-type soybean trypsin inhibitor.

2. The method of claim 1, wherein said composition is applied at least once daily on a continuous basis.

3. The method of claim 1, wherein said composition is applied at least twice daily for at least eight weeks and at least once daily on a continuous basis thereafter.

4. The method of claim 1, wherein said composition comprises 0.05-80% by weight of said soy product and is applied for at least four to ten weeks followed by topical application of a composition comprising 0.01-20% by weight of said soy product on a daily basis thereafter.

5. The method of claim 1, wherein said composition further comprises a cosmetically acceptable vehicle.

6. The method of claim 1, wherein said composition further comprises at least one anti-inflammatory agent.

7. The method of claim 1, wherein said composition further comprises at least one anti-cancer agent.

8. The method of claim 1, wherein said composition further comprises at least one anti-oxidant.

9. The method of claim 1, wherein said composition further comprises at least one sunscreen.

10. The method of claim 1, wherein said non-denatured, soy product is soy bean milk, wherein said composition comprises from about 1 to about 99%, by weight, of said soy bean milk, and wherein said composition further comprises from about 0.1 to about 20% emulsifier and a preservative in an effective amount.

11. The method of claim 10 wherein said composition further comprises an anti-oxidant.

12. The method of claim 10, wherein said composition further comprises an anti-cancer agent.

13. The method claim 10, wherein said composition further comprises at least one agent selected from the group consisting of anti-oxidants, sunscreens, moisturizers, bleaching agents, depigmentation agents, darkening agents, surfactants, foaming agents, conditioners, humectants, fragrances, anti-aging agents, anti-inflammatory agents, and anti-cancer agents.

14. The method of claim 1, wherein said non-denatured, soy product is soy bean powder or soy milk powder, wherein said composition comprises from about 0.1 to about 20%, by weight, of said soy bean powder or soy milk powder, and wherein said composition further comprises from about 0.1 to about 20% emulsifier and a preservative in an effective amount.

15. The method of claim 14, wherein said composition further comprises an anti-cancer agent.

16. The method of claim 14, wherein said composition further comprises an anti-oxidant.

17. The method of claim 14, wherein said composition further comprises at least one compound selected from the group consisting of anti-oxidants, sunscreens, moisturizers, bleaching agents, depigmentation agents, darkening agents, surfactants, foaming agents, conditioners, humectants, fragrances, anti-aging agents, anti-inflammatory agents, and anti-cancer agents.

* * * * *